US010364417B2

(12) United States Patent
Liu et al.

(10) Patent No.: US 10,364,417 B2
(45) Date of Patent: Jul. 30, 2019

(54) INCREASED ALCOHOL TOLERANCE USING THE PNTAB GENE

(71) Applicants: The United States of America, as represented by the Secretary of Agriculture, Washington, DC (US); The Regents of the University of California, Davis, CA (US)

(72) Inventors: Siqing Liu, Dunlap, IL (US); Christopher D. Skory, Washington, IL (US); David A. Mills, Davis, CA (US)

(73) Assignees: The United States of America, as Represented by the Secretary of Agriculture, Washington, DC (US); The Regents of the University of California, Davis, CA (US)

( * ) Notice: Subject to any disclaimer, the term of this patent is extended or adjusted under 35 U.S.C. 154(b) by 0 days.

(21) Appl. No.: 15/677,679

(22) Filed: Aug. 15, 2017

(65) Prior Publication Data

US 2019/0055525 A1 Feb. 21, 2019

(51) Int. Cl.
*C12N 1/20* (2006.01)
*C12N 9/02* (2006.01)

(52) U.S. Cl.
CPC .... *C12N 9/0036* (2013.01); *C12Y 106/01002* (2013.01)

(58) Field of Classification Search
CPC .................................................... C12N 9/0036
See application file for complete search history.

(56) References Cited

U.S. PATENT DOCUMENTS 5,424,202 A * 6/1995 Ingram ................ C12N 9/0006 435/161
2012/0005773 A1 * 1/2012 Aasen ................ C12N 15/8261 800/275

OTHER PUBLICATIONS

Makarova et al (PNAS USA vol. 103 (42) pp. 15611-15616) (Year: 2006).*
Anderlund et al (Applied and Environmental Microbiology vol. 65, No. 6, pp. 2333-2340) (Year: 1999).*
Clarke et al (Journal of Bacteriology vol. 162, No. 1, pp. 367-373) (Year: 1985).*
Alexandre et al.,"*Saccharomyces cerevisiae*—Oenococcus oeni interactions in wine: current knowledge and perspectives", International Journal of Food Microbiology, (2004) 93:141-154.
Bokhorst-van de Veen et al., "Short- and Long-Term Adaptation to Ethanol Stress and Its Cross-Protective Consequences in Lactobacillus plantarum," Applied and Environmental Microbiology, (2011), 77(15): 5247-5256.
Frazier et al., "Genetic Manipulation of Lactococcus lactis by Using Targeted Group II Introns: Generation of Stable Insertions without Selection" Applied and Environmental Microbiology, (2003), 69(2): 1121-1128.
Ingram, "Adaptation of Membrane Lipids to Alcohols," Journal of Bacteriology, (1976), 125(2): 670-678.
Liu, "Proteomic analyses of ethanol tolerance in Lactobacillus buchneri NRRL B-30929," Proteomics, (2014), pp. 2540-2544.
Liu et al., "Antibacterial activity of a cell wall hydrolase from Lactobacillus paracasei NRRL B-50314 produced by recombinant Bacillus megaterium," (2015), J Ind Microbiol Biotechnol, 42:229-235.
Liu et al., "Complete Genome Sequence of Lactobacillus buchneri NRRL B-30929, a Novel Strain from a Commercial Ethanol Plant," Journal of Bacteriology, (2011), 193(15):4019-4020.
Liu et al., "Lactobacillus buchneri strain NRRL B-30929 converts a concentrated mixture of xylose and glucose into ethanol and other products," J Ind Microbiol Biotechnol, (2008), 35:75-81.
Malherbe et al., "Comparative metabolic profling to investigate the contribution of O. oeni MLF starter cultures to red wine composition," J. Ind Microbiol Biotechnolo., (2012), 39:477-494.
Mills et al,Genomic analysis of Oenococcus oeni PSU-1 and , its relevance to winemaking, FEMS Microbiology Reviews 29, (2005), pp. 465-475.
Oddone et al., "Incorporation of nisl-mediated nisin immunity improves vector-based nisin-controlled gene expression in lactic acid bacteria," Plasmid, (2009), 61:151-158.
Pedersen et al., "Proton-translocating transhydrogenase: an update of unsolved and controversial issues", J Bioenerg Biomembr, (2008), 40:463-473.
Silveira et al., "Effect of Adaptation to Ethanol on Cytoplasmic and Membrane Protein Profiles of Oenococcus oeni", Applied and Environmental Microbiology, (2004), 70(5):2748-2755.
Ze-Ze et al., "The Oenococcus oeni genome: physical and genetic mapping of strain GM and comparison with the genome of a 'divergent' strain, PSU-1," Microbiology, (2000), 146: 3195-3204.

* cited by examiner

*Primary Examiner* — Albert M Navarro
(74) *Attorney, Agent, or Firm* — John Fado; Ariel Atkinson

(57) ABSTRACT

The pntAB locus may provide for increased alcohol tolerance in a microorganism, through expression of one or both of the pntA and pntB genes. A microorganism may have increased alcohol tolerance due to a transformation of the microorganism or an ancestor of the microorganism utilizing one or both of the pntA and pntB genes. The microorganism may be, for example, of a bacterial or fungal species. According to some exemplary embodiments, the microorganism may be a lactic acid bacterium.

20 Claims, 6 Drawing Sheets
(6 of 6 Drawing Sheet(s) Filed in Color)

Specification includes a Sequence Listing.

INCREASED ALCOHOL TOLERANCE USING THE PNTAB GENE

BACKGROUND

Bacterial envelope, plasma membrane, and cell surface-associated proteins are the prime contact point of bacteria with their environment. Thus, the cell envelope composition and stress-induced changes are thought to be significantly related to the ability of bacteria to survive in a diverse environment. When bacterial cells are exposed to increased ethanol or butanol concentrations, some can survive and become ethanol or butanol tolerant. There are economic interests in studying bacterial ethanol tolerance particularly in wine making and in industrial ethanol fermentation. Strains that can tolerate higher ethanol or butanol concentrations are desired for industrial fermentation.

When bacterial cells are exposed to a high ethanol environment, changes to the outer envelopes and plasma membrane lipid bilayer have been reported (Ingram, L. O. 1976. Adaptation of membrane lipids to alcohols. J Bacteriol 125:670-8 and Malherbe, S., et al. 2012. Comparative metabolic profiling to investigate the contribution of *O. oeni* MLF starter cultures to red wine composition. J Ind Microbiol Biotechnol 39:477-94) and the protein expression profiles of both membrane proteins as well as cellular proteins were adjusted in response to ethanol (Liu, S. 2014. Proteomic analyses of ethanol tolerance in *Lactobacillus buchneri* NRRL B-30929. Proteomics 14:2540-4). Previous studies of bacterial isolates of the fuel ethanol production facilities suggested that species of lactic acid bacteria are commonly found. Changes in membrane lipid composition and fatty acid biosynthesis pathways have been shown by transcriptome analyses of *Lactobacillus plantarum* cells gown for 24 hours in 8% ethanol and changes of cytoplasmic and membrane proteins have also been reported in ethanol tolerant *Oenococcus oeni* cells grown in 8% ethanol (van Bokhorst-van de Veen, H., et al. Short- and long-term adaptation to ethanol stress and its cross-protective consequences in *Lactobacillus plantarum*. Appl Environ Microbiol 77:5247-56; and Silveira, M. G., et al. 2004. Effect of adaptation to ethanol on cytoplasmic and membrane protein profiles of *Oenococcus oeni*. Appl Environ Microbiol 70:2748-55). However, due to technical difficulties in obtaining a sufficient amount of membrane proteins, a comprehensive proteomics study of integral membrane proteins has not been possible.

Ethanol tolerance of *Lactobacillus buchneri* NRRL B-30929 strain has been first described in 2008 (Liu, S., et al. 2008. *Lactobacillus buchneri* strain NRRL B-30929 converts a concentrated mixture of xylose and glucose into ethanol and other products. J. Ind Microbiol Biotechnol 35:75-81). This strain *L. buchneri* NRRL B-30929, isolated from an ethanol production plant, was described as tolerant up to a 14% ethanol concentration in its growth environment. Further comparative 2D gel electrophoresis studies of proteins isolated from cells grown in media containing 10% ethanol vs. 0% ethanol revealed that a total of 308 protein spots were either up- or down-regulated by ethanol exposure. However, only 20 proteins (11 increased, 9 decreased) were identified in response to a 10% ethanol by proteomics analyses (Liu, S., et al. 2011. Complete genome sequence of *Lactobacillus buchneri* NRRL B-30929, a novel strain from a commercial ethanol plant. J. Bacteriol 193:4019-4020).

The traditional wine making process uses selected lactic acid bacteria to convert malic acid to lactic acid to reduce wine acidity after yeast alcoholic fermentation either via natural process or man-made inoculation. The malolactic fermentation (MLF) cannot only improve the wine stability, but can also enhance aroma, flavor, and taste attributed to the fermentative production of metabolic intermediates, and is therefore a desired and sought after trait.

*O. oeni* is regarded as one of the best malolactic bacteria that can survive the harsh winemaking conditions, especially the higher ethanol contents, and this species had therefore been the subject of numerous studies for its applications to enhance wine quality and aroma by producing a range of volatile aroma compounds such as diacetyl, acetoin and 2,3-butanediol (Alexandre, H., et al. 2004. *Saccharomyces cerevisiae-Oenococcus oeni* interactions in wine: current knowledge and perspectives. Int. J. Food Microbiol. 93:141-54 and Malherbe, 2012). Nevertheless ethanol tolerance is one of the essential criteria for developing malolactic fermentation strains to be introduced in the wine making process and further exploration regarding the ethanol tolerance trait of *O. oeni* is still important.

All of the references cited herein, including U.S. Patents and U.S. Patent Application Publications, are incorporated by reference in their entirety.

Mention of trade names or commercial products in this publication is solely for the purpose of providing specific information and does not imply recommendation or endorsement by the U.S. Department of Agriculture.

SUMMARY

According to at least one exemplary embodiment, a transformed microorganism may contain an alcohol tolerance gene and have a higher alcohol tolerance as compared to a non-transformed microorganism, and the alcohol tolerance gene is one of pntAB, pntA, and pntB.

According to a further embodiment, the transformed microorganism may be one of a lactic acid bacterium and *Escherichia coli*.

According to a further embodiment, the alcohol tolerance gene may include the nucleotide sequence of one of SEQ ID NO: 17, SEQ ID NO: 18, SEQ ID NO: 19, SEQ ID NO: 20, SEQ ID NO: 21, and SEQ ID NO: 22.

According to a further embodiment, the alcohol tolerance gene may include a nucleotide sequence having at least 75% similarity to one of SEQ ID NO: 17, SEQ ID NO: 18, SEQ ID NO: 19, SEQ ID NO: 20, SEQ ID NO: 21, and SEQ ID NO: 22.

According to a further embodiment, the microorganism may express at least one alcohol tolerance protein, the alcohol tolerance protein being at least one of PntA and PntB.

According to yet a further embodiment, the alcohol tolerance protein may include the amino acid sequence of one of SEQ ID NO: 23, SEQ ID NO: 24, SEQ ID NO: 25, and SEQ ID NO: 26.

According to yet a further embodiment, the alcohol tolerance protein may include an amino acid sequence having at least 75% similarity to one of SEQ ID NO: 23, SEQ ID NO: 24, SEQ ID NO: 25, and SEQ ID NO: 26.

According to a further embodiment, the alcohol in which the transformed microorganism exhibits higher tolerance as compared to a non-transformed microorganism may be one of ethanol, propanol, and butanol.

According to a further embodiment, a microorganism including an alcohol tolerance gene, the alcohol tolerance gene being one of pntAB, pntA, and pntB may be a progeny of the transformed microorganism.

According to another exemplary embodiment, a method of making a transformed microorganism having high alcohol tolerance may include transforming a parental microorganism with a vector containing a DNA sequence encoding an alcohol tolerance gene, the alcohol tolerance gene being one of pntAB, pntA, and pntB and thereby obtaining a transformed microorganism containing the alcohol tolerance gene, and the transformed microorganism has a higher alcohol tolerance than the parental microorganism.

According to a further embodiment, the parental microorganism may be one of a lactic acid bacterium and *Escherichia coli.*

According to a further embodiment, the alcohol in which the transformed microorganism exhibits higher tolerance as compared to parental microorganism may be one of ethanol, propanol, and butanol.

According to another exemplary embodiment, an isolated DNA sequence may consist essentially of a nucleotide sequence having at least 95% identity to one of SEQ ID NO: 18, SEQ ID NO: 19, SEQ ID NO: 21, and SEQ ID NO: 22.

According to another exemplary embodiment, an expression vector may include a promoter and a heterologous polynucleotide, the heterologous polynucleotide encodes one or more proteins, the one or more proteins being at least one of PntA and PntB, and the promoter is operatively linked to said heterologous polynucleotide.

SEQUENCE LISTING

The Sequence Listing submitted via EFS-Web as an ASCII compliant text file format (.txt) filed Aug. 15, 2017, named "Sequence_Listing_019516" (created on Aug. 11, 2017, 33 kb), is hereby incorporated herein by reference in its entirety. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

SEQUENCES

The invention can be more fully understood from the following detailed description and the accompanying sequence descriptions, which form a part of this application.

SEQ ID NO: 1
GGGGACCGGTGAAAGGAGTTTTATGGCAATT is the OoTHF(AgeI) primer.

SEQ ID NO: 2
GGGGCCTAGGTTATTGATTAATATATTCTTTTGTCGAAG is the OoTHR(AvrII) primer.

SEQ ID NO: 3
ACCAACTCTTTTTATTTCCTAGGTTATTG is the THOF primer.

SEQ ID NO: 4
AGGTCGCGACCGGTGAAAG is the THOR primer.

SEQ ID NO: 5
GGGATAGTAATTCATTCCTGGTTG is the pMP3535H3 F1 primer.

SEQ ID NO: 6
CGGGCCCGTTATTTGTCTATG is the pMP3535H3 R1 primer.

SEQ ID NO: 7
TAAGAAGGAGATATACCATGGCAATTGTAGTTTCCGCTCT is the OopntA5'lic primer.

SEQ ID NO: 8
GTGGTGGTGGTGCTCGAATTATTCAGCCTCCTTTTTATC is the OopntA3'lic primer.

SEQ ID NO: 9
TAAGAAGGAGATATACCATGAGTACTTTAGAAACGATCGCCT is the OopntB5'lic primer.

SEQ ID NO: 10
GTGGTGGTGGTGCTCGAATTGATTAATATATTCTTTTGTCGAA is the OopntB3'lic primer.

SEQ ID NO: 11
TAAGAAGGAGATATACCATGTCTACGATTATTGCTGCTTTG is the LbpntA5'lic primer.

SEQ ID NO: 12
GTGGTGGTGGTGCTCGAATCCCCCTTCTCAGCTGATTT is the LbpntA3'lic primer.

SEQ ID NO: 13
TAAGAAGGAGATATACCATGTCACTCCTTAAAACGATT is the LbpntB5'lic primer.

SEQ ID NO: 14
GTGGTGGTGGTGCTCGAAATCTAAATACCCCTTGGTAGCCGC is the LbpntB3'Lic primer.

SEQ ID NO: 15
CCCGCGAAATTAATACGACTCAC is the pET28Gib5' primer.

SEQ ID NO: 16
GCTTCCTTTCGGGCTTTGTTAG is the pET28bGib3' primer.

SEQ ID NO: 17
TCGTAAAAACGTTTGCAAGAAATTGCGACGAAAGGTGAATC

GTGAAAGGAGTTTTATGGCAATTGTAGTTTCCGCTCTAAAAGAAGCTGCTGGTGAGA

-continued

ATCGTGTCGCATTGACCCCCGATGTTGTCGCCAAGCTGGTTAAGAGCAATTTTGATG

TTGTTATCGAAAAAGGAGCCGGAGAAAAAGCATTTTATTCCGATGATGTTTATAAGA

GTGCCGGCGCCAAGTTGTCAACCAGAACAGATGCTTTAAAAGCAGATATCGTGACG

GTCGTCAACGAACCGTCGACGGCAACTTTAAACAAATTGACGAAAGGTCAAACAAT

TATTGGGATGTTGAATCCTTTGGGGGACAAAAAAGCAGTTGAAAGTTTAGCGAAGG

CCGGAGTTACTTCTTTAGCTTTCGAACTGCTTCCACGAACGGTTTCCCGCGCCCAAA

ATTTGGATGCAAATTCATCGCAAAAATCGATTGCAGGATACAAAGCAGCTTTGTTAG

CTGCTGATACTTATCCGCAATATTTTCCGATGATGATGACGGCGGCCGGAACGGCTC

GTCCGGCTAAAGTACTTGTTATTGGCGCAGCTGTCGCTGGTTTGCAGGCAATCGGAA

CTGCTCATCGTTTGGGGGCGGTAGTTTCCGGCTACGATATCCGTGAGGATGCTCGCG

GCCAGGTTGAATCCTTAGGAGCAACGGCTTTGATTTCCGGCGTTCAGGTGAAAGATG

AAAATGGCTATGCTCGTGCTTTGACAACAGATGAGAAGAAAGCGCAGCAGACTGAA

CTGGAAGGCTTTATTGCTGAAAATAATGTCATTATCACTACAGCTCAAGTACCTGGT

GGAAAGCCTCCGGTCGTGGTTTCCAAAAAAGCTGTAGATAATGCTAAAGCCGGAAC

AGTCTTCATCGATCTTGGTTCGTCAGCTCTCGGCGGTAATGTTGAAGGTTCCAAGCCT

GGAGAGACAGTAGTAACTAAAAGCGGTGCTTTGATTGTGGGCGCCGGTGATTTGGC

AAGTCGTTTGCCAAAATCTTCCTCTGACATGTATGCGAAAAACGTTCAAAATACAAT

TAATTACATTATCAAGGATGGAAAAATTTTGCTCGATTTGGACGATGATGTTCTAAC

TGATCTCGTTGCTACTTACAAAGGAGAGATTTCTTCCAACTTCTTACGGAGCCGATTT

GGTTTGGAAAAACGTGTTGCTCAGAAAAAGACGGAAGATAAAAAGGAGGCTGAAT

AATGAGTGAAGAATTATATGCCAATTTAGCGATCTTTGTTTTGAGTTTGCTGGTTGGT

TTTGAAGTTATGTCGAAGATCCCTTCTACCTTGCAAACGCCGATGATGTCGGGAGCA

AATGCGATTCATGGAGTTGTTGTCGTGGGTGCTTTTGCGATTGCCGCCGAAGCTAAT

AATTGGCTTCTCTATATTCTGGTCTTCTTTGCTGCCTTATTTGCCGCAATCAATGTTTC

CGGAGGCTATACAGTCACGGATCGTATGTTGGGCATGTTTGATCGCAAACCATCCGA

CAAAAAGGAGGCAGATAAATGAGTACTTTAGAAACGATCGCCTCTTTGGTTTATCTT

GTTTCGGCATTTTGTTATGTGATCGGTGTTCACTTAATGCGTAGTCCAAAGACTGCTA

AAAATGGTAACCGTCTATCATTCGTCGGAATGATTTTAGCCGTTATTATGATTCTGTT

TCAATTAATCAGTTCCGGAAGGGTTCAAGCGACTGCATGGATTGTGTTGCTGGCTGG

CCTGCTGCTTGGAATAATTTATGGTGTTATGCGGGCCAGAAAAGTTCCAATGACTGA

TGTCCCGCAACTTGTTTCTTTGTTTAATGCCGTTGGTGGCGGTGCTGCTGCTGTTATT

GGTGTTTTTGATTATGTAACTGCATCCGGTCATTTAAGCCTTATTTTATCAATTCCGG

TTGTTTTGGATGTAATCATTGGTGGAATTACTTTCTCCGGTTCTTTGATTGCAACTGG

TAAACTTTCCGGAAAAGTTTCCGGGAAACCAATTAATTTCCCTGGTGCAAAAGTGAT

CAATATTTTGGTTGTAATTGCAATTGTAATTGCTGCCTTTCTGATGATTTCTGGTACG

GAAAATCCTTGGTATCTTTTGTTGGCTTTGTTTGCCAGCCTGATTTTCGGTCTGTTGA

TGACTCTGCCGATTGGTGGTGCTGACATGCCGGTGGTTGTTTCTTTACTGAATGCTTT

TACTGGTTTAGCAGTGGCTTTTGCCGGCTTTGTAATTGATAATCAGGTTTTGATTATT

GCTGGTGCTTTAGTTGGTGCCGCCGGTACAATCTTGACCCTGCAAATGGCCGATGCA

ATGAACCGTTCGGTGGCGAATATTTTGGCTGGTGGTTTTGGAACCGGCGATTCGGAG

TCTTCTTCGGCCTCCGATGGAGCCCCGGTTAAAGTTACAGAAACTTCGGCTGATGAT

-continued

ATTGGCCTTCAGCTGGCTTATGCTCACAATGTGATGATTGTTCCCGGTTATGGGCTTG

CTGCCGCCCAGGCACAACATGAAGTGGCCGAATTGGCAAAACTGTTGACTGATAAT

GGCATTAATGTTGACTATGCGATTCACCCGGTTGCTGGTCGTATGCCGGGACACATG

AATGTTTTACTGGCTGATGTCAATGTTCCTTATGGCCAGCTGAAACAGCTTGATGAT

GCAAATTCAATGTTTACCAATACGGACGTTTCTTTGGTAATTGGTGCAAACGATGTT

ACCAATCCGTTGGCTCGCGAGTCCGGTAATCCAATTTCTGGAATGCCAATCCTCGAT

GTTGACAAGTCAAAATCGGTTGTTGTTATTAAGCGTTCAATGAGCACTGGTTACGCC

GGCGTTCAAAATCCGTTATTCTCCTTGGATAACACAAAAATGTTCTTCGCCGATGCC

AAGAAAGGTCTTCAGGACATTATCGCTTCGACAAAAGAATATATTAATCAATAATTG

ATTAATATAAATATTATTAAAATCGTCTTTTACTGAAGACGATTTT is the whole transhydrogenase gene from *O. oeni* (OopntAB).

SEQ ID NO: 18

ATGGCAATTGTAGTTTCCGCTCTAAAAGAAGCTGCTGGTGA

GAATCGTGTCGCATTGACCCCCGATGTTGTCGCCAAGCTGGTTAAGAGCAATTTTGA

TGTTGTTATCGAAAAAGGAGCCGGAGAAAAAGCATTTTATTCCGATGATGTTTATAA

GAGTGCCGGCGCCAAGTTGTCAACCAGAACAGATGCTTTAAAAGCAGATATCGTGA

CGGTCGTCAACGAACCGTCGACGGCAACTTTAAACAAATTGACGAAAGGTCAAACA

ATTATTGGGATGTTGAATCCTTTGGGGGACAAAAAAGCAGTTGAAAGTTTAGCGAA

GGCCGGAGTTACTTCTTTAGCTTTCGAACTGCTTCCACGAACGGTTTCCCGCGCCCA

AAATTTGGATGCAAATTCATCGCAAAAATCGATTGCAGGATACAAAGCAGCTTTGTT

AGCTGCTGATACTTATCCGCAATATTTTCCGATGATGATGACGGCGGCCGGAACGGC

TCGTCCGGCTAAAGTACTTGTTATTGGCGCAGCTGTCGCTGGTTTGCAGGCAATCGG

AACTGCTCATCGTTTGGGGGCGGTAGTTTCCGGCTACGATATCCGTGAGGATGCTCG

CGGCCAGGTTGAATCCTTAGGAGCAACGGCTTTGATTTCCGGCGTTCAGGTGAAAGA

TGAAAATGGCTATGCTCGTGCTTTGACAACAGATGAGAAGAAAGCGCAGCAGACTG

AACTGGAAGGCTTTATTGCTGAAAATAATGTCATTATCACTACAGCTCAAGTACCTG

GTGGAAAGCCTCCGGTCGTGGTTTCCAAAAAAGCTGTAGATAATGCTAAAGCCGGA

ACAGTCTTCATCGATCTTGGTTCGTCAGCTCTCGGCGGTAATGTTGAAGGTTCCAAG

CCTGGAGAGACAGTAGTAACTAAAAGCGGTGCTTTGATTGTGGGCGCCGGTGATTTG

GCAAGTCGTTTGCCAAAATCTTCCTCTGACATGTATGCGAAAAACGTTCAAAATACA

ATTAATTACATTATCAAGGATGGAAAAATTTTGCTCGATTTGGACGATGATGTTCTA

ACTGATCTCGTTGCTACTTACAAAGGAGAGATTTCTTCCAACTTCTTACGGAGCCGA

TTTGGTTTGGAAAAACGTGTTGCTCAGAAAAAGACGGAAGATAAAAAGGAGGCTGA

A is the *O. oeni* pntA gene (OopntA).

SEQ ID NO: 19

ATGAGTACTTTAGAAACGATCGCCTCTTTGGTTTATCTTGTTT

CGGCATTTTGTTATGTGATCGGTGTTCACTTAATGCGTAGTCCAAAGACTGCTAAAA

ATGGTAACCGTCTATCATTCGTCGGAATGATTTTAGCCGTTATTATGATTCTGTTTCA

ATTAATCAGTTCCGGAAGGGTTCAAGCGACTGCATGGATTGTGTTGCTGGCTGGCCT

GCTGCTTGGAATAATTTATGGTGTTATGCGGGCCAGAAAAGTTCCAATGACTGATGT

CCCGCAACTTGTTTCTTTGTTTAATGCCGTTGGTGGCGGTGCTGCTGCTGTTATTGGT

-continued

GTTTTTGATTATGTAACTGCATCCGGTCATTTAAGCCTTATTTTATCAATTCCGGTTG

TTTTGGATGTAATCATTGGTGGAATTACTTTCTCCGGTTCTTTGATTGCAACTGGTAA

ACTTTCCGGAAAAGTTTCCGGGAAACCAATTAATTTCCCTGGTGCAAAAGTGATCAA

TATTTTGGTTGTAATTGCAATTGTAATTGCTGCCTTTCTGATGATTTCTGGTACGGAA

AATCCTTGGTATCTTTTGTTGGCTTTGTTTGCCAGCCTGATTTTCGGTCTGTTGATGAC

TCTGCCGATTGGTGGTGCTGACATGCCGGTGGTTGTTTCTTTACTGAATGCTTTTACT

GGTTTAGCAGTGGCTTTTGCCGGCTTTGTAATTGATAATCAGGTTTTGATTATTGCTG

GTGCTTTAGTTGGTGCCGCCGGTACAATCTTGACCCTGCAAATGGCCGATGCAATGA

ACCGTTCGGTGGCGAATATTTTGGCTGGTGGTTTTGGAACCGGCGATTCGGAGTCTT

CTTCGGCCTCCGATGGAGCCCCGGTTAAAGTTACAGAAACTTCGGCTGATGATATTG

GCCTTCAGCTGGCTTATGCTCACAATGTGATGATTGTTCCCGGTTATGGGCTTGCTGC

CGCCCAGGCACAACATGAAGTGGCCGAATTGGCAAAACTGTTGACTGATAATGGCA

TTAATGTTGACTATGCGATTCACCCGGTTGCTGGTCGTATGCCGGGACACATGAATG

TTTTACTGGCTGATGTCAATGTTCCTTATGGCCAGCTGAAACAGCTTGATGATGCAA

ATTCAATGTTTACCAATACGGACGTTTCTTTGGTAATTGGTGCAAACGATGTTACCA

ATCCGTTGGCTCGCGAGTCCGGTAATCCAATTTCTGGAATGCCAATCCTCGATGTTG

ACAAGTCAAAATCGGTTGTTGTTATTAAGCGTTCAATGAGCACTGGTTACGCCGGCG

TTCAAAATCCGTTATTCTCCTTGGATAACACAAAAATGTTCTTCGCCGATGCCAAGA

AAGGTCTTCAGGACATTATCGCTTCGACAAAAGAATATATTAATCAA is the *O. oeni* pntB gene (OopntB).

SEQ ID NO: 20

ATGTCTACGATTATTGCTGCTTTGAAGGAATCTGGCGATGA

AAACCGTGTGGCAATCACACCGGATGTGGCTGCGAAATTAGTTCACAGCAAGTTTG

AAGTTATGATCGAACAGGGCGCTGGTCAGAATGCTTATTTTTCTGACCAGGCCTACC

AAGATGCTGGCGCAAAAGTCGTTAGCCGAGACGATGCAGTTAGTCAGGCCAATGTG

ATTGCGACGGTTGATTTACCTGATTCAGAGACTTTGGGCAAGTTGCATGAGGGACAG

ATTTTAATTGGCTTGTTGAAGGCCTTGACCGATTTGGACTCGGTGCAAAAACTTGCT

AAACAGAAGGTCACGGCGCTGTCGTTTGAACTGCTGCCGCGGACCATTTCCCGTGCC

CAAAGCATGAATGTCTTAAGTTCACAAGCCTCAATTGCCGGTTACAAAGCTGCTTTG

GTGGCTGCTGACAAATTCGCCCGTTATTTCCCAATGATGATCACTGCTGCGGGGACT

GCCAAGCCTGCCAAAGTGTTGGTCTTAGGGACCGGAGTTGCCGGCCTGCAAGCCATT

GGAACTGCCAAACGGCTGGGGGCAATTGTTTCCGGTTATGATGTTCGTCCAGCGTCT

CGAGGCGAAGTTGAATCACTCGGTGCCGAATTTCTCACTAGTTCAGTCAGTGCTGTC

GGTGAAGGCGGTTATGCCCGTCAATTGTCTGCTGATGAGCAAAAGCAGCAGCAAGA

CGAATTAATTGGGTTTATCAAACAAAATGATATTGTCATCACCACCGCGCAGGTTCC

TGGAAGAAAGCCGCCACTGCTGGTTCCTCAAGCCGCCGTTGATAACGCTAAACCAG

GTAGCGTCTTCGTTGATTTGGCTGCCAGTGATTTGGGTGGTAATGTCGCTGGATCAA

AGCCCGACCAAACAGTGATCACTGATTCCGGTGTTCAACTGATTGGGGCCGGGAATT

TAGCCAGTGAAATGGCAACGTCGGCTTCTGAAATGTTCTCTAAGAACGTTCAGGCAG

TGATTAATGATGTTGCTGATAAGGATGCTCAAATTACCATCGATTTAAAAGATGACG

TAATGAGCCAATTGGTTGCGACCGACCATGGCGAAATTATTTCTGAACGAGTCAGAA

-continued

AAGCGCTGAACCTGCCAATTTCAAAACCGGCTGAAGACGATGCTGCCCCTGCCGATT

CTGACGACAAATCAGCTGAGAAGGGGGATTAGTCATTATGAGTCAAGAATTATATA

CGAATTTAGCCATTTTTGTTTTGAGCCTGCTAGTTGGGTTTGAAGTTATGAGTAAAAT

TCCCTCAACCCTGCAGACGCCAATGATGTCTGGTGCCAATGCGATTCATGGCGTCGT

CGTTGTCGGTGCCTTTGTGATTGCTGCAGAAGCCAGCAGCTGGTATTTCTACCTGTTG

GCATTTCTAGCCGCATTCTTTGCAGCTGTCAACGTCGCCGGTGGTTACACCGTGACT

GACCGGATGCTGGGAATGTTTAACCGGCCGAAAAAACAGCCGAATTCAGCTGACAA

GGGAGGCGACAAATAATGTCACTCCTTAAAACGATTGCTTCCCTAATTTACCTGCTG

TCAGCGGTCTGCTATGTGATTGGTGTTCACATGATGCGCTCCCCAAAGACGGCTCGG

AATGGTAATTTACTTTCCGGACTTGGGATGGCCATGGCAGTTGTCATGATTTTAGTTG

AAATTATCTCCAAGGGTCAGATTACCTTAATTGGCTGGACGGTATTGTTTGCGGGTC

TGTTAATCGGAATTTTGTATGGAGTTATCCGCGCACGCAAAGTGCCAATGACCGATG

TTCCTCAATTGGTTTCGCTGTTTAACGCCGTTGGTGGCGGTGCCGCTGCCACAATCGG

GATTTTCGATTACACCCACGAAGCTGTCGGTACCTCTTTGAGCCTGGCCTTTTCCATT

CCAGTGCTGCTTGACATTATTATTGGTGGGATTACCTTCTCAGGCTCGCTAATTGCAA

CCGGTAAATTGTCCGGACATGTGCCCGGCAAACCAATTTCGTTTCCCGGCGACAAAT

TGATTAACGGTCTGGCAGTGTTAGCAATTATCGTTGCCGGTGTTTGGATGATTGGTTT

TCCTTCCGCTTACTGGCCTATGGTACTGGCATTGTTAGCCAGTTTGATTTTTGGCCTA

TTGATGACCTTGCCAATTGGTGGTGCCGACATGCCGGTGGTTGTTTCACTTTTGAACG

CCTTTACCGGTTTGGCGGTTGCCTTTGCCGGATTTGTCATTGATAATCAGGTCTTGAT

TATCGCTGGTGCGCTGGTTGGTGCGGCCGGAACAATTTTGACCCTGCAAATGGCCGA

AGCAATGAACCGATCAGTTGCCAACATTATTGCTGGCGGCTTCGGTAGTGGCGATTC

CAACGGCAGTATTGGTGCGGGTGCTGAGGTGCCAACCAACATTAAGAAGACCACAC

CCGATGATGTCGGCATGCAGCTGGCCTATGCGCACAATGTCATGATCGTTCCCGGTT

ATGGTTTGGCTGCCGCTCAGGCTCAGCATGAAGTCGCTGAGTTGGCGAAATTGCTGA

CGGATGCCGGAATTAACGTCAACTATGCGATTCACCCAGTTGCCGGCCGGATGCCTG

GCCATATGAACGTTTTGCTCGCCGATGTCAACGTTCCTTACGATCAAATGAAACAGT

TGGATGAAGCCAACTCGATGTTTGAAAATACTGACGTTTCGCTGGTTATTGGCGCTA

ACGATGTTACCAATCCATTGGCTCGTGAAAAGGGTAACGCCATTTCGGGGATGCCAA

TTTTGGATGTTGATAAATCAAAGTCCGTCGTTGTCATTAAGCGTTCCATGAGTACCG

GTTACGCCGGTGTTCAAAACCCACTGTTTAGTGAAGATCAGACCAGTATGATGTTCT

CGGATGCCAAGAAGGGGCTGCAGGAAATTATTGCGGCTACCAAGGGGTATTTAGAT

TAA is the whole transhydrogenase gene from *L. buchneri* (LbpntAB).

SEQ ID NO: 21

ATGTCTACGATTATTGCTGCTTTGAAGGAATCTGGCGATGAA

AACCGTGTGGCAATCACACCGGATGTGGCTGCGAAATTAGTTCACAGCAAGTTTGA

AGTTATGATCGAACAGGGCGCTGGTCAGAATGCTTATTTTTCTGACCAGGCCTACCA

AGATGCTGGCGCAAAAGTCGTTAGCCGAGACGATGCAGTTAGTCAGGCCAATGTGA

TTGCGACGGTTGATTTACCTGATTCAGAGACTTTGGGCAAGTTGCATGAGGGACAGA

TTTTAATTGGCTTGTTGAAGGCCTTGACCGATTTGGACTCGGTGCAAAAACTTGCTA

AACAGAAGGTCACGGCGCTGTCGTTTGAACTGCTGCCGCGGACCATTTCCCGTGCCC

-continued

AAAGCATGAATGTCTTAAGTTCACAAGCCTCAATTGCCGGTTACAAAGCTGCTTTGG

TGGCTGCTGACAAATTCGCCCGTTATTTCCCAATGATGATCACTGCTGCGGGGACTG

CCAAGCCTGCCAAAGTGTTGGTCTTAGGGACCGGAGTTGCCGGCCTGCAAGCCATTG

GAACTGCCAAACGGCTGGGGGCAATTGTTTCCGGTTATGATGTTCGTCCAGCGTCTC

GAGGCGAAGTTGAATCACTCGGTGCCGAATTTCTCACTAGTTCAGTCAGTGCTGTCG

GTGAAGGCGGTTATGCCCGTCAATTGTCTGCTGATGAGCAAAAGCAGCAGCAAGAC

GAATTAATTGGGTTTATCAAACAAAATGATATTGTCATCACCACCGCGCAGGTTCCT

GGAAGAAAGCCGCCACTGCTGGTTCCTCAAGCCGCCGTTGATAACGCTAAACCAGG

TAGCGTCTTCGTTGATTTGGCTGCCAGTGATTTGGGTGGTAATGTCGCTGGATCAAA

GCCCGACCAAACAGTGATCACTGATTCCGGTGTTCAACTGATTGGGGCCGGGAATTT

AGCCAGTGAAATGGCAACGTCGGCTTCTGAAATGTTCTCTAAGAACGTTCAGGCAGT

GATTAATGATGTTGCTGATAAGGATGCTCAAATTACCATCGATTTAAAAGATGACGT

AATGAGCCAATTGGTTGCGACCGACCATGGCGAAATTATTTCTGAACGAGTCAGAA

AAGCGCTGAACCTGCCAATTTCAAAACCGGCTGAAGACGATGCTGCCCCTGCCGATT

CTGACGACAAATCAGCTGAGAAGGGGGA is the *L. buchneri* pntA gene (LbpntA).

SEQ ID NO: 22

ATGTCACTCCTTAAAACGATTGCTTCCCTAATTTACCTGCTGT

CAGCGGTCTGCTATGTGATTGGTGTTCACATGATGCGCTCCCCAAAGACGGCTCGGA

ATGGTAATTTACTTTCCGGACTTGGGATGGCCATGGCAGTTGTCATGATTTTAGTTGA

AATTATCTCCAAGGGTCAGATTACCTTAATTGGCTGGACGGTATTGTTTGCGGGTCT

GTTAATCGGAATTTTGTATGGAGTTATCCGCGCACGCAAAGTGCCAATGACCGATGT

TCCTCAATTGGTTTCGCTGTTTAACGCCGTTGGTGGCGGTGCCGCTGCCACAATCGG

GATTTTCGATTACACCCACGAAGCTGTCGGTACCTCTTTGAGCCTGGCCTTTTCCATT

CCAGTGCTGCTTGACATTATTATTGGTGGGATTACCTTCTCAGGCTCGCTAATTGCAA

CCGGTAAATTGTCCGGACATGTGCCCGGCAAACCAATTTCGTTTCCCGGCGACAAAT

TGATTAACGGTCTGGCAGTGTTAGCAATTATCGTTGCCGGTGTTTGGATGATTGGTTT

TCCTTCCGCTTACTGGCCTATGGTACTGGCATTGTTAGCCAGTTTGATTTTTGGCCTA

TTGATGACCTTGCCAATTGGTGGTGCCGACATGCCGGTGGTTGTTTCACTTTTGAACG

CCTTTACCGGTTTGGCGGTTGCCTTTGCCGGATTTGTCATTGATAATCAGGTCTTGAT

TATCGCTGGTGCGCTGGTTGGTGCGGCCGGAACAATTTTGACCCTGCAAATGGCCGA

AGCAATGAACCGATCAGTTGCCAACATTATTGCTGGCGGCTTCGGTAGTGGCGATTC

CAACGGCAGTATTGGTGCGGGTGCTGAGGTGCCAACCAACATTAAGAAGACCACAC

CCGATGATGTCGGCATGCAGCTGGCCTATGCGCACAATGTCATGATCGTTCCCGGTT

ATGGTTTGGCTGCCGCTCAGGCTCAGCATGAAGTCGCTGAGTTGGCGAAATTGCTGA

CGGATGCCGGAATTAACGTCAACTATGCGATTCACCCAGTTGCCGGCCGGATGCCTG

GCCATATGAACGTTTTGCTCGCCGATGTCAACGTTCCTTACGATCAAATGAAACAGT

TGGATGAAGCCAACTCGATGTTTGAAAATACTGACGTTTCGCTGGTTATTGGCGCTA

ACGATGTTACCAATCCATTGGCTCGTGAAAAGGGTAACGCCATTTCGGGGATGCCAA

TTTTGGATGTTGATAAATCAAAGTCCGTCGTTGTCATTAAGCGTTCCATGAGTACCG

GTTACGCCGGTGTTCAAAACCCACTGTTTAGTGAAGATCAGACCAGTATGATGTTCT

-continued

CGGATGCCAAGAAGGGGCTGCAGGAAATTATTGCGGCTACCAAGGGGTATTTAGAT is the *L. buchneri* pntB gene (LbpntB).

SEQ ID NO: 23

MAIVVSALKEAAGENRVALTPDVVAKLVKSNFDVVIEKGAGEK

AFYSDDVYKSAGAKLSTRTDALKADIVTVVNEPSTATLNKLTKGQTIIGMLNPLGDKKA

VESLAKAGVTSLAFELLPRTVSRAQNLDANSSQKSIAGYKAALLAADTYPQYFPMMMT

AAGTARPAKVLVIGAAVAGLQAIGTAHRLGAVVSGYDIREDARGQVESLGATALISGV

QVKDENGYARALTTDEKKAQQTELEGFIAENNVIITTAQVPGGKPPVVVSKKAVDNAK

AGTVFIDLGSSALGGNVEGSKPGETVVTKSGALIVGAGDLASRLPKSSSDMYAKNVQNT

INYIIKDGKILLDLDDDVLTDLVATYKGEISSNFLRSRFGLEKRVAQKKTEDKKEAE is the *O. oeni* PntA protein, corresponding to the nucleotide sequence in SEQ ID NO: 18 above.

SEQ ID NO: 24

MSTLETIASLVYLVSAFCYVIGVHLMRSPKTAKNGNRLSFVGM

ILAVIMILFQLISSGRVQATAWIVLLAGLLLGIIYGVMRARKVPMTDVPQLVSLFNAVGG

GAAAVIGVFDYVTASGHLSLILSIPVVLDVIIGGITFSGSLIATGKLSGKVSGKPINFPGAK

VINILVVIAIVIAAFLMISGTENPWYLLLALFASLIFGLLMTLPIGGADMPVVVSLLNAFTG

LAVAFAGFVIDNQVLIIAGALVGAAGTILTLQMADAMNRSVANILAGGFGTGDSESSSA

SDGAPVKVTETSADDIGLQLAYAHNVMIVPGYGLAAAQAQHEVAELAKLLTDNGINVD

YAIHPVAGRMPGHMNVLLADVNVPYGQLKQLDDANSMFTNTDVSLVIGANDVTNPLA

RESGNPISGMPILDVD KSKSVVVIKRSMSTGYAGVQNPLFSLDNTKMFFADAKKGLQDII

ASTKEYINQ is the *O. oeni* PntB protein, corresponding to the nucleotide sequence in SEQ ID NO: 19 above.

SEQ ID NO: 25

MSTIIAALKESGDENRVAITPDVAAKLVHSKFEVMIEQGAGQN

AYFSDQAYQDAGAKVVSRDDAVSQANVIATVDLPDSETLGKLHEGQILIGLLKALTDLD

SVQKLAKQKVTALSFELLPRTISRAQSMNVLSSQASIAGYKAALVAADKFARYFPMMIT

AAGTAKPAKVLVLGTGVAGLQAIGTAKRLGAIVSGYDVRPASRGEVESLGAEFLTSSVS

AVGEGGYARQLSADEQKQQQDELIGFIKQNDIVITTAQVPGRKPPLLVPQAAVDNAKPG

SVFVDLAASDLGGNVAGSKPDQTVITDSGVQLIGAGNLASEMATSASEMFSKNVQAVIN

DVADKDAQITIDLKDDVMSQLVATDHGEIISERVRKALNLPISKPAEDDAAPADSDDKS

AEKGD is the *L. buchneri* PntA protein, corresponding to the nucleotide sequence in SEQ ID NO: 21 above.

SEQ ID NO: 26

MSLLKTIASLIYLLSAVCYVIGVHMMRSPKTARNGNLLSGLG

MAMAVVMILVEIISKGQITLIGWTVLFAGLLIGILYGVIRARKVPMTDVPQLVSLFNAVG

GGAAATIGIFDYTHEAVGTSLSLAFSIPVLLDIIIGGITFSGSLIATGKLSGHVPGKPISFPGD

KLINGLAVLAIIVAGVWMIGFPSAYWPMVLALLASLIFGLLMTLPIGGADMPVVVSLLN

AFTGLAVAFAGFVIDNQVLIIAGALVGAAGTILTLQMAEAMNRSVANIIAGGFGSGDSN

GSIGAGAEVPTNIKKTTPDDVGMQLAYAHNVMIVPGYGLAAAQAQHEVAELAKLLTD

AGINVNYAIHPVAGRMPGHMNVLLADVNVPYDQMKQLDEANSMFENTDVSLVIGAND

VTNPLAREKGNAISGMPILDVDKSKSVVVIKRSMSTGYAGVQNPLFSEDQTSMMFSDAK

-continued

```
KGLQEIIAATKGYLD is the L. buchneri PntB protein, corresponding

to the nucleotide sequence in SEQ ID NO: 22 above.
```

BRIEF DESCRIPTION OF THE FIGURES

Advantages of embodiments of the present invention will be apparent from the following detailed description of the exemplary embodiments. The patent or application file contains at least one drawing executed in color. Copies of this patent or patent application publication with color drawing(s) will be provided by the office upon request and payment of the necessary fee. The following detailed description should be considered in conjunction with the accompanying figures in which.

Exemplary

Exemplary

Exemplary

Exemplary

Exemplary

Exemplary

Exemplary

DETAILED DESCRIPTION

Figure 1:
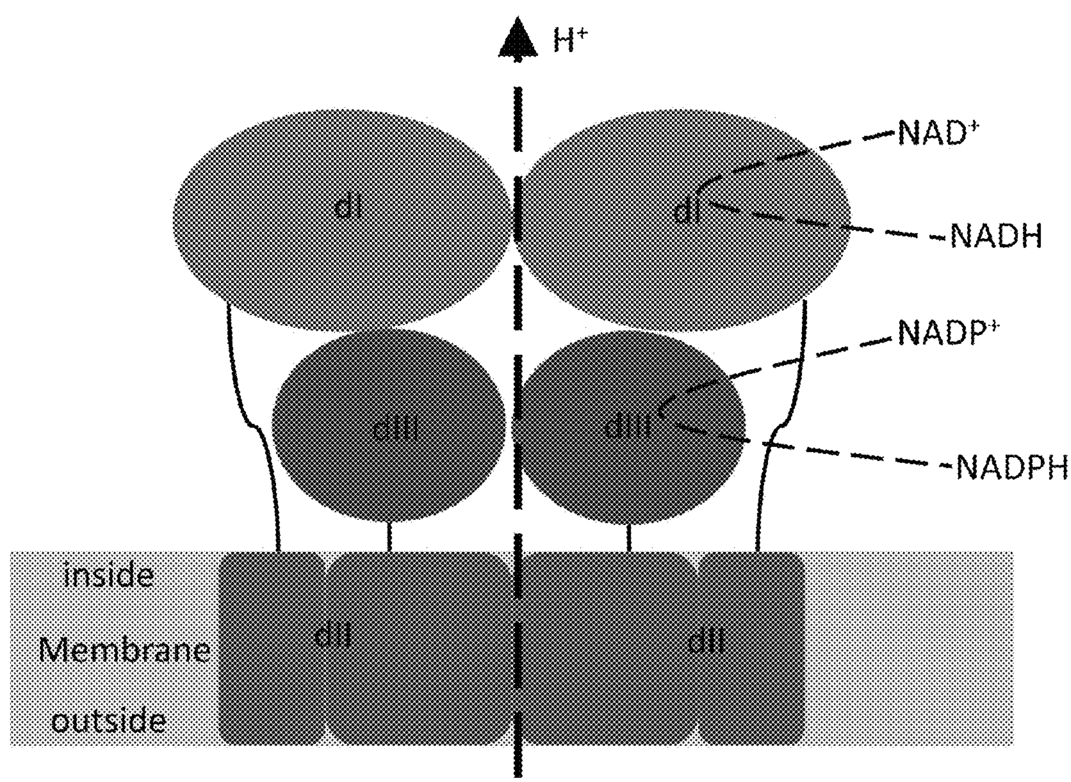
FIG. 1 shows a schematic diagram of transhydrogenase and its proton-translocating reaction of PntA and PntB protein complex in *O. oeni* and *L. buchneri.*

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention," "embodiments," or "invention" do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

The term "consisting essentially of" excludes additional steps or composition components that substantially interfere with the intended activity of the method or composition, and can be readily determined by those skilled in the art, for example from a consideration of this specification or practice of the invention disclosed herein.

The amounts, percentages, and ranges disclosed herein are not meant to be limiting, and increments between the recited amounts, percentages, and ranges are specifically envisioned as part of the invention.

This invention utilizes routine techniques in the field of molecular biology. Unless otherwise noted, technical terms are used according to conventional usage.

"Cloning" means the selection and propagation of (a) genetic material from a single individual, (b) a vector containing one gene or gene fragment, or (c) a single organism containing one such gene or gene fragment.

A "cloning vector" is a plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

A "codon" is a DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

"Complement or complementary sequence" refers to the product of complementary base pairing in which purines bond with pyrimidines, as it occurs in the two polynucleotide chains of DNA (adenine with thymine, guanine with cytosine) and between DNA and messenger RNA nucleotides during transcription. The "complement" of a particular polynucleotide sequence is thus that nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A< >T; G< >C) and reading in the 5' to 3' direction, i.e., in opposite direction of the represented nucleotide sequence (reverse complement).

A "DNA coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, prokaryotic sequences and cDNA from eukaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

"Expression" refers to the process undergone by a structural gene to produce a polypeptide. Expression requires both transcription of DNA and translation of RNA.

An "expression vector" or "vector" is a replicon such as a plasmid, virus, retrovirus, bacteriophage, or nucleic acid sequence which is introduced to and able to replicate in a host cell, and may be characterized by a restriction endonuclease recognition site at which the sequence may be cut in a predetermined fashion for the insertion of a heterologous DNA sequence. An expression vector may have a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase, which binds the promoter sequence transcribes the coding sequence into mRNA which is then in turn translated into the protein encoded by the coding sequence.

A "gene" is a segment of DNA which encodes a specific protein or polypeptide, or RNA.

"Genome" means the entire DNA of an organism. It includes, among other things, the structural genes encoding for the polypeptides of the substance, as well as operator, promoter and ribosome binding and interaction sequences.

"Heterologous DNA" is a DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

"Hybridization" is the pairing together or annealing of single stranded regions of nucleic acids to form double-stranded molecules.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA," "RNA," "polynucleotides," "polynucleotide sequence," "oligonucleotide," "nucleic acid," "nucleic acid sequence," "nucleic acid fragment," and "isolated nucleic acid fragment" are used interchangeably herein.

A "nucleotide" is a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsulated in a protein envelope or coat ("capsid"). In a unicellular organism, a phage may be introduced by a process called transfection.

A "plasmid" is a non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant."

Polypeptide. A linear series of amino acids connected one to the other by peptide bonds between the alpha-amino and carboxy groups of adjacent amino acids.

The term "primer" refers to an oligonucleotide, which is capable of acting as a point of initiation of synthesis when placed under conditions in which primer extension is initiated. A primer may occur naturally, as in a purified restriction digest, or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant viruses may express genes/polynucleotides that are not found within the native (non-recombinant or wild-type) form of the viruses or express native genes in an otherwise abnormal amount—over-expressed, under-expressed or not expressed at all—compared to the non-recombinant or wild-type sequence, polynucleotide, or organism.

The terms "transgenic," "transformed," "transformation," and "transfection" are similar in meaning to "recombinant." "Transformation," "transgenic," and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants," as well as recombinant organisms or cells.

The "start codon," also called the "initiation codon," is the first mRNA triplet to be translated during protein or peptide synthesis and immediately precedes the structural gene being translated. The start codon is usually AUG, but may sometimes also be GUG.

A "structural gene" is a DNA sequence which encodes through its template or messenger RNA (mRNA) a sequence of amino acids characteristic of a specific polypeptide.

mentary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. Table 1, infra, contains information about which nucleic acid codons encode which amino acids and is useful for determining the possible nucleotide substitutions that are included in this invention.

TABLE 1

| Amino acid | Nucleic acid codons | Amino acid | Nucleic acid codons |
|---|---|---|---|
| Ala/A | GCT, GCC, GCA, GCG | Leu/L | TTA, TTG, CTT, CTC, CTA, CTG |
| Arg/R | CGT, CGC, CGA, CGG, AGA, AGG | Lys/K | AAA, AAG |
| Asn/N | AAT, AAC | Met/M | ATG |
| Asp/D | GAT, GAC | Phe/F | TTT, TTC |
| Cys/C | TGT, TGC | Pro/P | CCT, CCC, CCA, CCG |
| Gln/Q | CAA, CAG | Ser/S | TCT, TCC, TCA, TCG, AGT, AGC |
| Glu/E | GAA, GAG | Thr/T | ACT, ACC, ACA, ACG |
| Gly/G | GGT, GGC, GGA, GGG | Trp/W | TGG |
| His/H | CAT, CAC | Tyr/Y | TAT, TAC |
| Ile/I | ATT, ATC, ATA | Val/V | GTT, GTC, GTA, GTG |
| Stop | TAA, TGA, TAG | | |

"Substantially pure" refers to the condition of a compound, such as a protein or a nucleotide, being cell free or being separated from other components that would interfere with or have a substantial qualitative effect on the activity of the compound or on a substrate on which the compound acts.

"Transform" refers to changing, in a heritable manner, the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In prokaryotes and some fungi, for example, the exogenous DNA may be maintained on an episomal element such as a plasmid. With respect to most eukaryotic cells, a stably transformed cell is one in which the exogenous DNA has been integrated into a chromosome so that it is inherited by daughter cells through chromosome replication. This stability is demonstrated by the ability of the eukaryotic cell to establish cell lines or clones comprised of a population of daughter cells containing the exogenous DNA.

"Transcription" is the process of producing mRNA from a structural gene.

"Translation" is the process of producing a polypeptide from mRNA.

For nucleic acids, sizes are given in either kilobases (kb) or base pairs (bp). Estimates are typically derived from agarose or polyacrylamide gel electrophoresis, from sequenced nucleic acids, from published DNA sequences, or other established techniques. For proteins, sizes are given in kilodaltons (kDa or KDa) or amino acid residue numbers. Proteins sizes are estimated from gel electrophoresis, sequenced proteins, derived amino acid sequences, published protein sequences, or other established techniques.

Unless otherwise indicated, a particular nucleic acid sequence for each amino acid substitution (alteration) also implicitly encompasses conservatively modified variants thereof (e.g., degenerate codon substitutions), the comple- In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 2 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

TABLE 2

| Amino Acid | Conservative Substitute |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |

TABLE 2-continued

| Amino Acid | Conservative Substitute |
|---|---|
| Gly | Ala |
| His | Asn, Arg, Gln, Glu |
| Ile | Leu, Val |
| Leu | Ile, Val |
| Lys | Arg, Gln, Glu |
| Met | Ile, Leu |
| Phe | His, Leu, Met, Trp, Tyr |
| Ser | Cys, Thr |
| Thr | Ser, Val |
| Trp | Phe, Tyr |
| Tyr | His, Phe, Trp |
| Val | Ile, Leu, Thr |

The terms "identical" or percent "identity", in the context of two or more polynucleotides or polypeptide sequences, refer to two or more sequences or sub-sequences that are the same or have a specified percentage of nucleotides or amino acids (respectively) that are the same (e.g., 80%, 85% identity, 90% identity, 99%, or 100% identity), when compared and aligned for maximum correspondence over a designated region as measured using a sequence comparison algorithm or by manual alignment and visual inspection.

The phrase "high percent identical" or "high percent identity", in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In an exemplary embodiment, a high percent identity exists over a region of the sequences that is at least about 16 nucleotides or amino acids in length. In another exemplary embodiment, a high percent identity exists over a region of the sequences that is at least about 50 nucleotides or amino acids in length. In still another exemplary embodiment, a high percent identity exists over a region of the sequences that is at least about 100 nucleotides or amino acids or more in length. In one exemplary embodiment, the sequences are high percent identical over the entire length of the polynucleotide or polypeptide sequences.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of various algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al. (eds.), *Current Protocols in Molecular Biology,* 1995 supplement).

According to at least one exemplary embodiment, one or more genes, specifically the pntA and pntB genes (collectively pntAB) may provide increased alcohol tolerance in a microorganism. According to at least another exemplary embodiment, a microorganism may have increased alcohol tolerance due to a transformation of the microorganism or an ancestor of the microorganism utilizing one or both of the pntA and pntB genes.

The increased alcohol tolerance of the present invention may refer to a transformed microorganism's greater ability to survive in an environment with a specific concentration of alcohol than a wild type of the microorganism. The alcohol could be any alcohol as determined by one of skill in the art. Examples of alcohols contemplated in this invention include, but are not limited to methanol, ethanol, propanol, butanol, and isomers thereof.

The microorganism which may be transformed in the present invention may be any microorganism which can be transformed by normal and/or known techniques. The microorganism may be, for example, of a bacterial or fungal species. According to some exemplary embodiments, the microorganism may be a lactic acid bacterium. The microorganism may be a species in Order Lactobacillales. Further, the microorganism may be a species in one or more genera, including, but not limited to, the genus of *Lactococcus.*

Methods and Materials

Bacterial Strains and Growth Conditions.

The *L. buchneri* NRRL B-30929 strain was previous isolated and characterized by USDA researchers (Liu 2008). The cells were cultured at 30° C. in MRS broth pH 6.5 with 110 rpm. *O. oeni* PSU-1 strain was growing at 28° C. in MTJ broth (50% MRS and 50% TJB) pH 5.5 (BD, Rockville Md.) as described in the literature (Ze-Ze, et al. 2000. The *Oenococcus oeni* genome: physical and genetic mapping of strain GM and comparison with the genome of a 'divergent' strain, PSU-1. Microbiology 146 Pt 12:3195-204). *Lactococcus lactis* IL-1403 was grown in M17 broth containing 0.5% glucose as described (Frazier, C. L., et al. 2003. Genetic manipulation of *Lactococcus lactis* by using targeted group II introns: generation of stable insertions without selection. Appl Environ Microbiol 69:1121-8). *Escherichia coli* DH5α and BL21(DE3)pLysS cells were grow in LB supplemented with ampicillin (amp 100 μg/ml) or kanamycin (kan 30.5 μg/ml) or chloramphenicol (chlor 34 μg/ml) when required.

Genomic PCR.

Genomic DNA from *L. buchneri* NRRL B-30929 and *O. oeni* PSU-1 was isolated as described previously (Liu, S., et al. 2011. Complete genome sequence of *Lactobacillus buchneri* NRRL B-30929, a novel strain from a commercial ethanol plant. J Bacteriol 193:4019-4020, and Mills, D. A., et al. 2005. Genomic analysis of *Oenococcus oeni* PSU-1 and its relevance to winemaking. FEMS Microbiol Rev 29:465-75). PCR primers, shown in Table 3 below, were designed based on the sequence flanking the transhydrogenase genes pntA & pntB from the *O. oeni* PSU-1 genome sequence (GenBank accession number NC_008528.1) and *L. buchneri* NRRL B-30929 (GenBank accession number CP002652).

TABLE 3

PCR and sequencing primers used in the Examples herein

| Primer Name | SEQ ID NO | Sequence |
|---|---|---|
| OoTHF (AgeI) | SEQ ID NO: 1 | GGGGACCGGTGAAAGGAGTTTATGGCAATT |
| OoTHR (AvrII) | SEQ ID NO: 2 | GGGGCCTAGGTTATTGATTAATATATTCTTTTGTCGAAG |
| THOF | SEQ ID NO: 3 | ACCAACTCTTTTTATTTCCTAGGTTATTG |
| THOR | SEQ ID NO: 4 | AGGTCGCGACCGGTGAAAG |
| pMP3535H3 F1 | SEQ ID NO: 5 | GGGATAGTAATTCATTCCTGGTTG |
| pMP3535H3 R1 | SEQ ID NO: 6 | CGGGCCCGTTATTTGTCTATG |
| OopntA5'lic | SEQ ID NO: 7 | TAAGAAGGAGATATACCATGGCAATTGTAGTTTCCGCTCT |
| OopntA3'lic | SEQ ID NO: 8 | GTGGTGGTGGTGCTCGAATTATTCAGCCTCCTTTTTATC |
| OopntB5'lic | SEQ ID NO: 9 | TAAGAAGGAGATATACCATGAGTACTTTAGAAACGATCGCCT |
| OopntB3'lic | SEQ ID NO: 10 | GTGGTGGTGGTGCTCGAATTGATTAATATATTCTTTTGTCGAA |
| LbpntA5'lic | SEQ ID NO: 11 | TAAGAAGGAGATATACCATGTCTACGATTATTGCTGCTTTG |
| LbpntA3'lic | SEQ ID NO: 12 | GTGGTGGTGGTGCTCGAATCCCCCTTCTCAGCTGATTT |
| LbpntB5'lic | SEQ ID NO: 13 | TAAGAAGGAGATATACCATGTCACTCCTTAAAACGATT |
| LbpntB3'Lic | SEQ ID NO: 14 | GTGGTGGTGGTGCTCGAAATCTAAATACCCCTTGGTAGCCGC |
| pET28Gib5' | SEQ ID NO: 15 | CCCGCGAAATTAATACGACTCAC |
| pET28bGib3' | SEQ ID NO: 16 | GCTTCCTTTCGGGCTTTGTTAG |

Genomic PCR, DNA purification, molecular cloning and transformation protocols in *E. coli* DH5α and BL21(DE3) pLysS cells were carried out as described previously (Liu, et al. 2015. Antibacterial activity of a cell wall hydrolase from *Lactobacillus paracasei* NRRL B-50314 produced by recombinant *Bacillus megaterium*. J. Ind. Microbiol. Biotechnol. 42:229-35).

Example 1: Identification of pntAB

The available genome sequences of *L. buchneri* NRRL B-30929 (Liu 2011) and *O. oeni* PSU-1 (Mills 2005) allowed the inventors to conduct comparative genomic analyses with other lactic acid bacteria (LAB) genomes. The data (unpublished) revealed that both ethanol tolerant strains *L. buchneri* and *O. oeni* possessed a dihydronicotinamide-adenine dinucleotide phosphate (NADPH) transhydrogenase system that were absent in almost all other LAB genomes. The NADPH transhydrogenases reduce NADP by NADH through hydride transfer driven by an electrochemical proton gradient. These proton-pumping transhydrogenases are one of the main sources of cytosolic NADPH and have been linked in mammalian systems to protection from oxidative stress.

The *O. oeni* transhydrogenase system comprises two genes, pntA and pntB, together termed pntAB, encoding the alpha and beta subunits arranged in an operon. The full length of the entire operon is around 3 Kb. DNA sequence and translated protein sequence analyses revealed that a PntA protein is translated from the first open reading frame from *O. oeni* pntA (Oeoe_0369, 1176 bp, 392 aa, SEQ ID NO:23) and the PntB protein is translated from the second open reading frame from *O. oeni* pntB (Oeoe_0371, 1413 bp, 470 aa, SEQ ID NO:24), and there is around 305 bp gap in between the two subunits. Similarly, the *L. buchneri* pntAB locus shared this arrangement, and there is also a 326 bp gap in the *L. buchneri* pntAB operon between LbpntA (Lbuc_1847, 1209 bp, 402 aa, SEQ ID NO:25) and LbpntB (Lbuc 1846, 1419 bp, 472 aa, SEQ ID NO:26).

The 1419 bp pntB gene from *L. buchneri* B-30929 has been identified and isolated and this gene shared 71.0% identity with the pntB from *O. oeni*. Also identified and isolated was the 1209 bp pntA gene from *L. buchneri* B-30929, but there is no significant shared similarity between the pntA DNA sequences from *L. buchneri* and *O oeni*. The PntB protein (472 aa) from *L. buchneri* shared 78.6% identity (91.9% similarity) with the PntB protein (470 aa) from *O. oeni* and the PntA protein (402 aa) from *L. buchneri* shared 58% identity and 77% similarity with the PntA protein (392 aa) from *O. oeni*. For the purposes of this invention, percent identity refers to the percentage of amino acids which are exactly the same between the two proteins, whereas percent similarity refers the percentage of amino acids which are either the same or functionally equivalent such that they would not substantially change the functional properties of the protein.

It is envisioned that the pntAB, pntA, and pntB genes and the corresponding PntA and PntB proteins, respectively, from other organisms also having high alcohol tolerance may be substituted for those disclosed herein. In addition, a gene having a high percent identity or high percent similarity (i.e. at least 75%) to the genes disclosed herein may have a similar functionality, as could be easily determined by one of ordinary skill in the art.

The schematic diagram of transhydrogenase and its proton-translocating reaction of PntA and PntB protein complex in *O. oeni* and *L. buchneri* are presented (FIG. 1). This is based on a structural model of NADP(H) proton-translocating transhydrogenase from *Escherichia coli* depicted by Pedersen et al (2008. Proton-translocating transhydrogenase: an update of unsolved and controversial issues. J Bioenerg Biomembr 40:463-73). The active form of transhydrogenase in *E. coli* was assembled in a tetramer of two subunits each. The pntA gene encodes the transmembrane (dII) helices 1-4, plus NAD(H)-binding domain (dI) and pntB gene encodes the helices 6-14 (dII) plus the NADP(H)-binding domain (dIII).

Example 2: Expression of OopntAB and Solvent Tolerance in Recombinant *L. lactis*

Introduction of the Transhydrogenase Locus in *L. lactis*.

Figure 2:
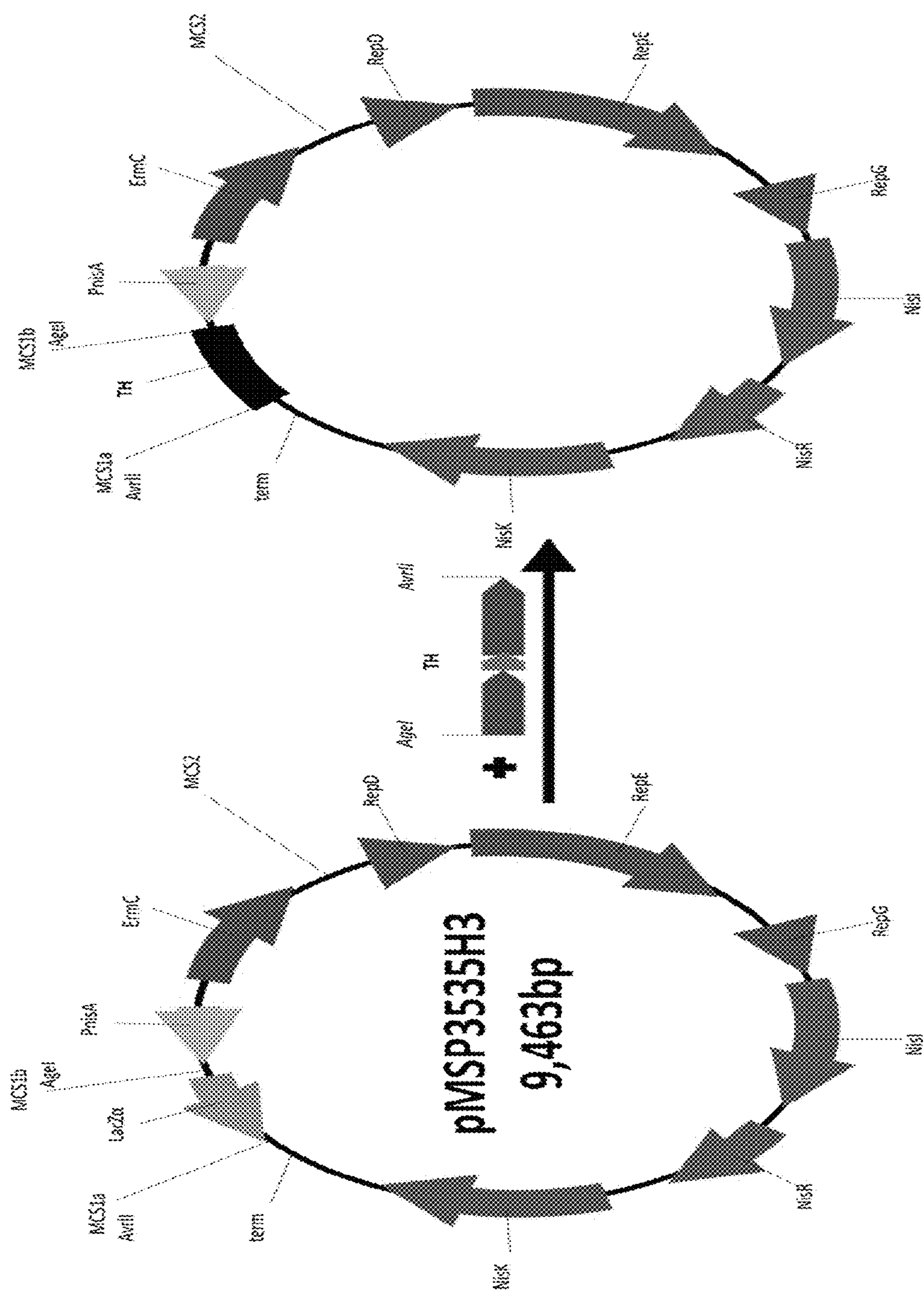
FIG. 2 shows a schematic representation of the creation of the pMSP3535H3-TH used to introduce recombinant genes into *L. lactis.*

The pMSP3535H3 vector (Oddone, G. M., et al. 2009. Incorporation of nisI-mediated nisin immunity improves vector-based nisin-controlled gene expression in lactic acid bacteria. Plasmid 61:151-8) was used to express the pntAB locus. The entire pntAB locus from *O. oeni* PSU-1 was amplified from genomic PCR using primers OoTHF and OoTHR (Table 3), which were designed specifically for the transhydrogenase gene of *O. oeni* PSU-1. Two unique restriction enzyme sites for AgeI and AvrII respectively were introduced in PCR primers so that the full length pntAB locus (about 3 Kb) was digested with AgeI and AvrII (New England Biolabs, Beverly, Mass.) and cloned into the pMSP3535H3 vector at the AgeI and AvrII sites to generate pMSP3535H3-TH (FIG. 2). After sequencing confirmation, the pMSP3535H3-TH was introduced in *L. lactis* and recombinant protein expression was induced by nisin addition in the media. The ligation mixture was transformed in *L. lactis* IL-1403 cells by electroporation using a Bio-Rad Pulser under the following conditions: 50 μL competent *L. lactis* IL1403 with 100-400 ng plasmid DNA loaded into a 0.1 cm cuvette (Bio-Rad, Hercules, Calif.), 1.8 kV potential, 8 hour recovery at 30° C. in 1 mL Difco M17 broth (BD, Franklin Lakes, N.J.) supplemented with 1% glucose (Fisher Chemical, Fairlawn, N.J.), and plating on agar of the same M17 glucose medium supplemented with 5 μg/mL erythromycin. Plasmid DNA isolation was carried out by using a QIAprep miniprep kit (Qiagen, CA). The positive clone pMSP3535H3-TH was confirmed by DNA Sequencing of the plasmid using the primers THOF and THOR (Table 1) via an ABI Prism 310 using a Dye Terminator Cycle Sequencing Kit (Applied Biosystems, Foster City, Calif.).

Tolerance Test.

The recombinant *L. lactis* cells were subjected to growth analyses in media with various concentrations of ethanol, butanol or isopropanol. To achieve this, *L. lactis* hosting pMSP3535H3 and pMSP3535H3-TH were grown in M17 broth containing 1% glucose, 10 μg/mL erythromycin, 100 ng/mL of nisin and concentrations of alcohol ranging from 1.4%-6.5%. The effects of growth of the recombinant bacteria carrying the transhydrogenase locus by selected alcohols were compared with that of the strain carrying control vector. Growth curves were obtained from triplicate readings with a Synergy 2 plate reader (BioTek, Winooski, Vt.). Each well contained 160 μL of recombinant *L. lactis* carrying either pMSP3535H3 (control) or pMSP3535H3-TH expressing the transhydrogenase and 30 μL of filter sterilized mineral oil. OD600 values were used to determine relative concentrations of cells in the wells.

Figure 3:
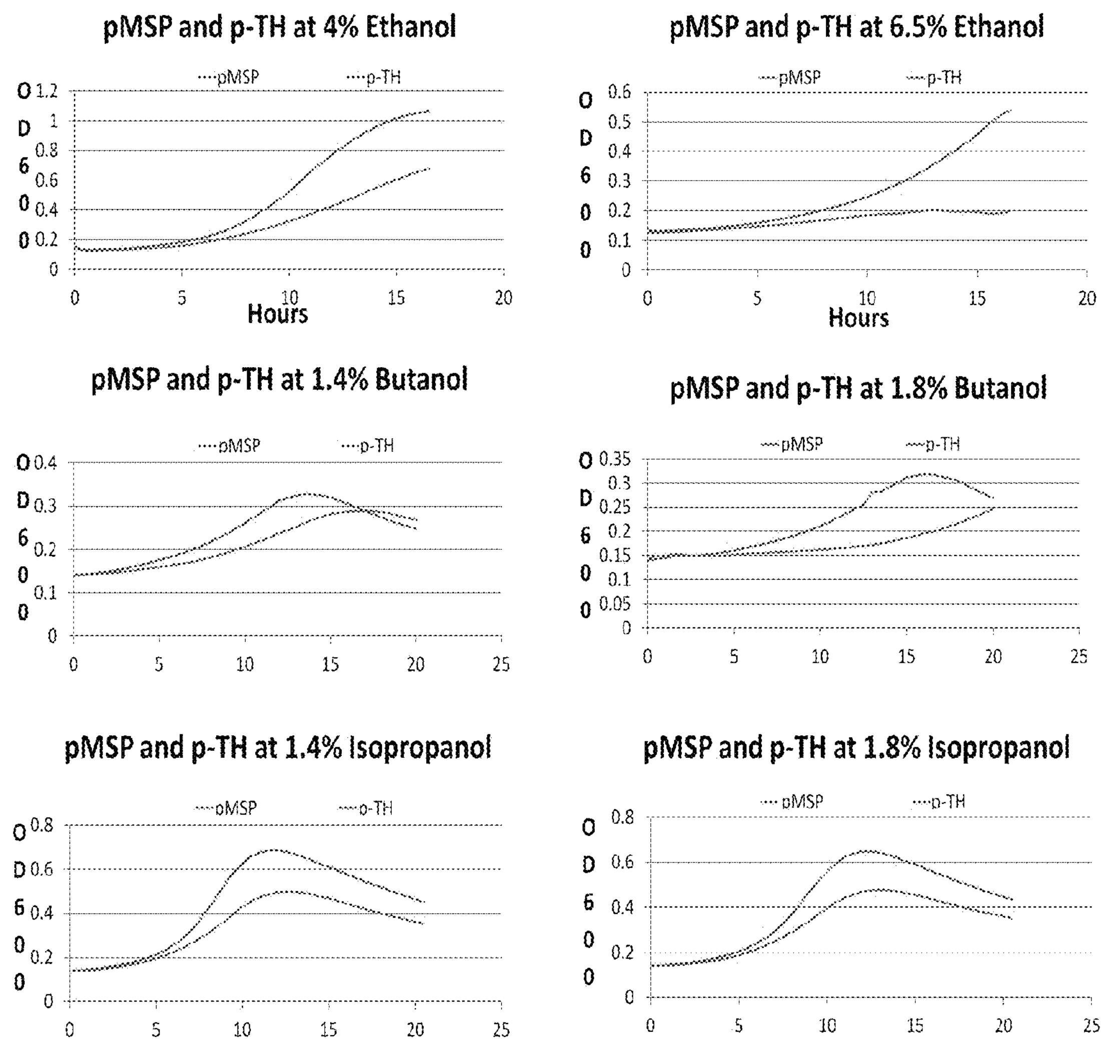
FIG. 3 shows growth analyses of *L. lactis* both under the condition of expression of pntAB (p-TH) and a control with no recombinant expression (pMSP).

Growth analyses presented in FIG. 3 indicate that the expression of pntAB in *L. lactis* improved tolerance to ethanol from 4% to 6.5%, tolerance to butanol from 1.4 to 1.8% and tolerance to isopropanol from 1.4 to 1.8% separately when compared with the growth of the control recombinant *L. lactis* strain carrying the pMSP3535H3 vector.

Example 3: Expression and Ethanol Tolerance of OopntB in *E. coli*

Transhydrogenase Overexpression in *Escherichia coli*.

To construct an individual clone pntB from *O. oeni* (OopntB), the Ligation Independent Cloning (LIC) method was used as instructed by vendor (New England Biolabs, Beverly, Mass.). Briefly, PCR reactions were carried out using pfx polymerase, pMSP3535H3-TH as template and the corresponding primer pairs (OopntB5'Lic and 3', Table 1). For vector treatment, standard PCR reaction was carried out with the pET28b plasmid as template, using pfx polymerase and specific pET28Gib5' and pET28Gib3'primers (Table 1). The PCR amplified pET28b vector was then digested with DpnI. All insert fragments and vector DNA were purified by using a Qiagen PCR purification kit and eluted in $H_2O$. Both target fragments and linearized vector were treated with T4 DNA polymerase, then OopntB gene fragments were separately annealed with the treated pET28b vector for 30 min at 37° C. The positive pET28b clones containing the individual gene including OopntB were introduced into *E. coli* BL21pLysS cells (NovaBlue GigaSingles, Novagen) and individual colonies on LB kan plates were picked for screening. All positive plasmid constructs were confirmed by DNA sequencing.

Ethanol Tolerance.

The recombinant *E. coli* BL21(DE3)pLysS cells expressing the individual OopntB gene were grown in 3 ml LB kan/chlor and grown at 37° C. at 220 rpm overnight. Then 200 μl of the overnight culture was inoculated into 12 ml LB kan/chlor and grown at 37° C. at 220 rpm until OD600 0.4-0.6 was achieved. Then IPTG was added to the media (to a final concentration of 1 mM) for induced expression for 2-6 hrs. The cells were grown in media either with or without ethanol.

Figure 4:
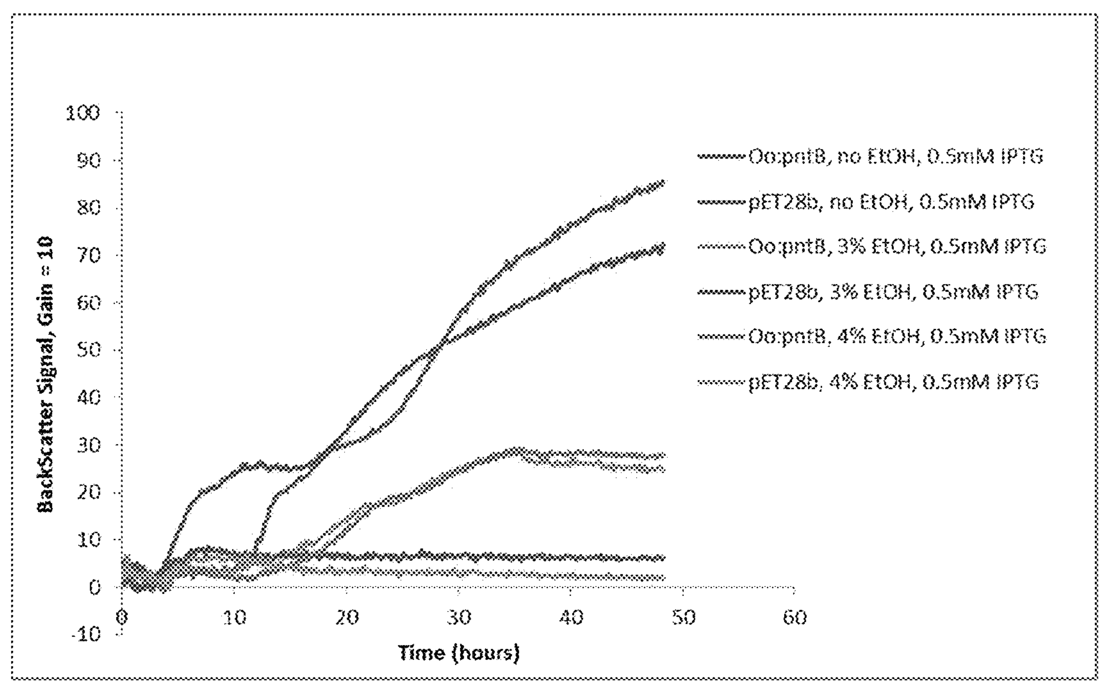
FIG. 4 shows the results of a biolector ethanol tolerance assay of recombinant *E. coli* carrying pET28bOopntB vs recombinant *E. coli* carrying a pET28b control vector.

The ethanol tolerance of recombinant strains was assessed by monitoring growth at 1000 rpm as reflected by the scattered light intensity using the BioLector system (m2p-labs, Baesweiler Germany). The data demonstrated that the recombinant *E. coli* carrying pET28bOopntB in LB with 3 and 4% ethanol displayed resistance to ethanol in the media when compared with of the recombinant *E. coli* carrying the pET28b empty vector (FIG. 4). The results demonstrated that the overexpression of OopntB enabled ethanol tolerance of the host *E. coli* cells in ethanol concentrations at least up to 4% when compared with the growth of recombinant *E. coli* carrying an empty pET28b vector.

Example 4: Expression and Ethanol Tolerance of LbpntB in *E. coli*

Expression and ethanol tolerance testing for LbpntB in *E. coli* was achieved using the same methods as described in Example 3, except that the corresponding primer pair was LbpntB5'Lic and 3' (Table 1) and LbpntB was used in place of OopntB (the LbpntB gene from *L. buchneri* having been PCR amplified from genomic DNA of *L. buchneri* NRRL B-30929).

Figure 5:
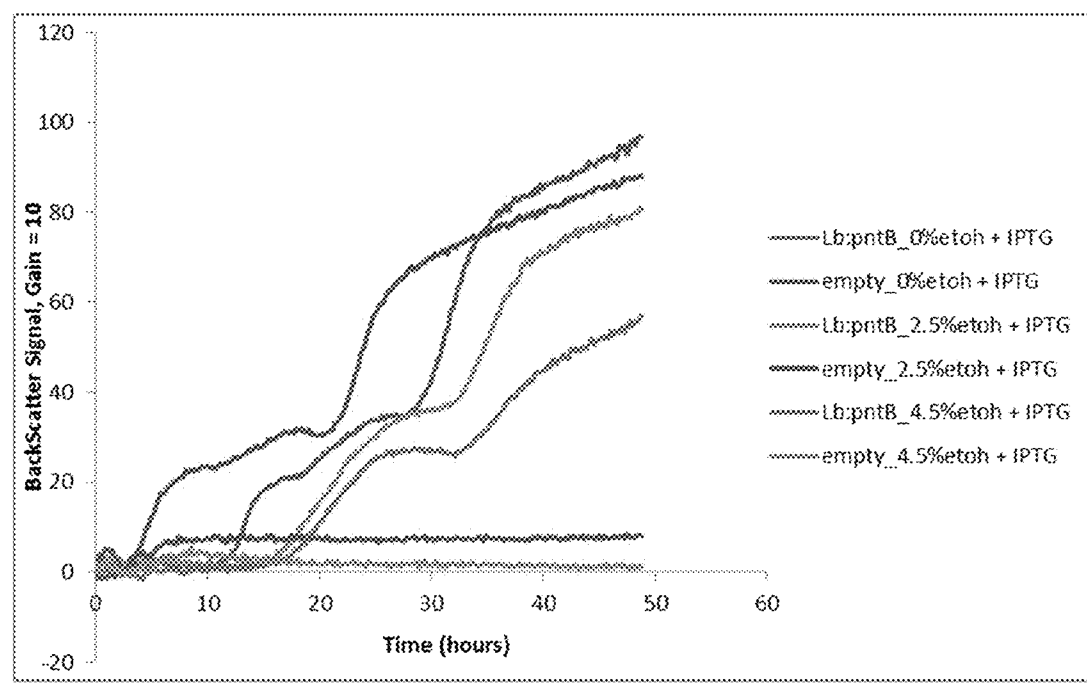
FIG. 5 shows the results of a biolector ethanol tolerance assay of recombinant *E. coli* carrying pET28bLbpntB. The results demonstrate higher tolerance (up to 4.5% ethanol) of recombinant *E. coli* that was conferred by pET28bLbpntB.

The ethanol tolerance data, shown in FIG. 5, show that the LbpntB gene is capable of improving ethanol tolerance of the host *E. coli* strain. The LbpntB gene conferred ethanol tolerance of the host cells when grow in LB media with 2.5% and 4.5% ethanol while the control carrying empty pET28b vector appeared ethanol sensitive. It was observed that both LbpntB and the empty vector grow well in 0% ethanol.

Example 5: Expression and Ethanol Tolerance of OopntA and LbpntA in *E. coli*

Expression and ethanol tolerance testing for OopntA and LbpntA in *E. coli* was achieved using the same methods as described in Examples 3 and 4, except that the corresponding primer pairs were OopntA5'lic and 3', and LbpntA5'Lic and 3' (Table 1), and OopntA and LbpntA were used in place of OopntB (Example 3) or LbpntB (Example 4).

Figure 6A:
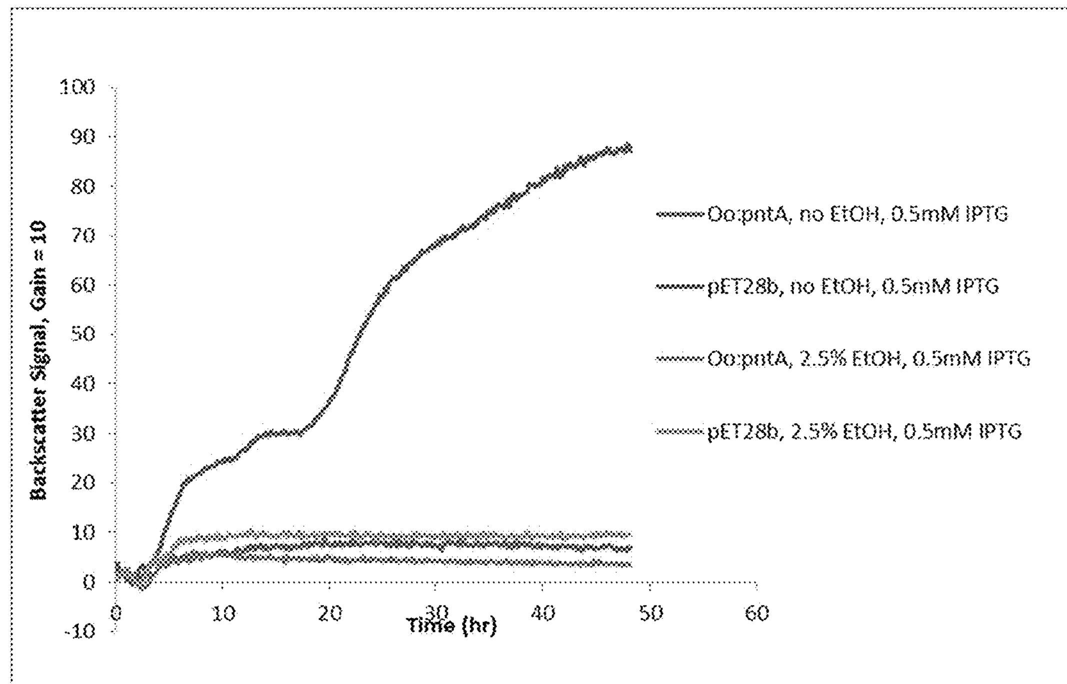
FIG. 6A shows the results of a biolector ethanol tolerance assay of recombinant *E. coli* carrying pET28bOopntA.
Figure 6B:
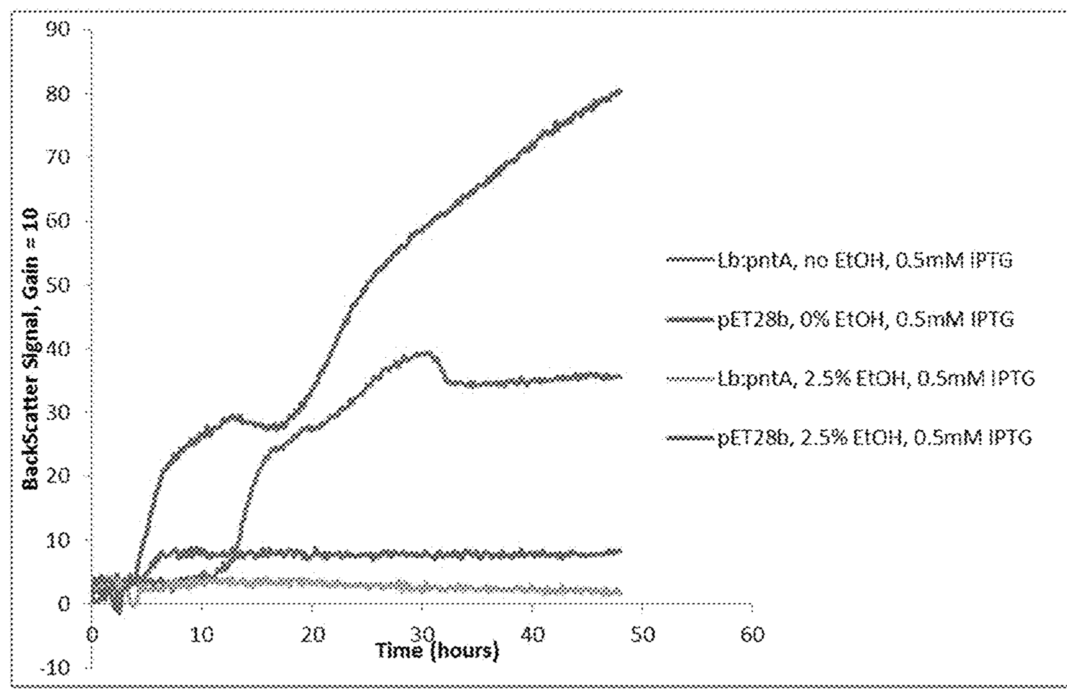
FIG. 6B shows the results of a biolector ethanol tolerance assay of recombinant *E. coli* carrying pET28bLbpntA.

The ethanol tolerance data, shown in FIGS. 6A and 6B, suggest that no significant ethanol tolerance is imparted in *E. coli* by either of OopntA and LbpntA, by themselves. Considering that there are no significant conserved DNA sequence similarities between the two pntA genes, it is hypothesized that the pntA gene plays a less significant role in contrast with that of the pntB gene.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A transformed microorganism, wherein the transformed microorganism contains an alcohol tolerance gene, wherein the transformed microorganism has a higher alcohol tolerance as compared to a non-transformed microorganism, and wherein the alcohol tolerance gene is one of pntAB, pntA, and pntB, wherein each of pntA, pntB, and pntAB is a transhydrogenase gene, wherein the alcohol tolerance gene comprises a nucleotide sequence having at least 75% similarity to one of SEQ ID NO: 17, SEQ ID NO: 18, SEQ ID NO: 19, SEQ ID NO: 20, SEQ ID NO: 21, and SEQ ID NO: 22, and wherein the microorganism expresses at least one alcohol tolerance protein, the alcohol tolerance protein being at least one of PntA and PntB.

2. The transformed microorganism of claim 1, wherein the microorganism is one of a lactic acid bacterium and *Escherichia coli*.

3. The transformed microorganism of claim 1, wherein the alcohol tolerance gene comprises the nucleotide sequence of one of SEQ ID NO: 17, SEQ ID NO: 18, SEQ ID NO: 19, SEQ ID NO: 20, SEQ ID NO: 21, and SEQ ID NO: 22.

4. A transformed microorganism, wherein the transformed microorganism contains an alcohol tolerance gene, wherein the transformed microorganism has a higher alcohol tolerance as compared to a non-transformed microorganism, and wherein the alcohol tolerance gene is one of pntAB, pntA, and pntB, wherein each of pntA, pntB, and pntAB is a transhydrogenase gene, wherein the microorganism expresses at least one alcohol tolerance protein, the alcohol tolerance protein being at least one of PntA and PntB, and wherein the alcohol tolerance protein comprises an amino acid sequence having at least 75% similarity to one of SEQ ID NO: 23, SEQ ID NO: 24, SEQ ID NO: 25, and SEQ ID NO: 26.

5. The transformed microorganism of claim 4, wherein the alcohol tolerance protein comprises the amino acid sequence of one of SEQ ID NO: 23, SEQ ID NO: 24, SEQ ID NO: 25, and SEQ ID NO: 26.

6. The transformed microorganism of claim 1, wherein the alcohol in which the transformed microorganism exhibits higher tolerance as compared to a non-transformed microorganism is one of ethanol, propanol, and butanol.

7. A microorganism comprising an alcohol tolerance gene, the alcohol tolerance gene being one of pntAB, pntA, and pntB, and wherein the microorganism is a progeny of the transformed microorganism of claim 1.

8. A method of making a transformed microorganism having high alcohol tolerance, comprising:

transforming a parental microorganism with a vector containing a DNA sequence encoding an alcohol tolerance gene, the alcohol tolerance gene being one of pntAB, pntA, and pntB; and thereby obtaining a transformed microorganism containing the alcohol tolerance gene, wherein each of pntA, pntB, and pntAB is a transhydrogenase gene, wherein the transformed microorganism has a higher alcohol tolerance than the parental microorganism, wherein the alcohol tolerance gene comprises a nucleotide sequence having at least 75% similarity to one of SEQ ID NO: 17, SEQ ID NO: 18, SEQ ID NO: 19, SEQ ID NO: 20, SEQ ID NO: 21, and SEQ ID NO: 22, and wherein the transformed microorganism expresses at least one of the alcohol tolerance proteins PntA and PntB.

9. The method of claim 8, wherein the parental microorganism is one of a lactic acid bacterium and *Escherichia coli*.

10. The method of claim 8, wherein the alcohol tolerance gene comprises the nucleotide sequence of one of SEQ ID NO: 17, SEQ ID NO: 18, SEQ ID NO: 19, SEQ ID NO: 20, SEQ ID NO: 21, and SEQ ID NO: 22.

11. A method of making a transformed microorganism having high alcohol tolerance, comprising:

transforming a parental microorganism with a vector containing a DNA sequence encoding an alcohol tolerance gene, the alcohol tolerance gene being one of pntAB, pntA, and pntB; and thereby obtaining a transformed microorganism containing the alcohol tolerance gene, wherein each of pntA, pntB, and pntAB is a transhydrogenase gene, wherein the transformed microorganism has a higher alcohol tolerance than the parental microorganism, wherein the transformed microorganism expresses at least one of the alcohol tolerance proteins PntA and PntB, and wherein the alcohol tolerance protein comprises an amino acid sequence having at least 75% similarity to one of SEQ ID NO: 23, SEQ ID NO: 24, SEQ ID NO: 25, and SEQ ID NO: 26.

12. The method of claim 11, wherein the alcohol tolerance protein comprises the amino acid sequence of one of SEQ ID NO: 23, SEQ ID NO: 24, SEQ ID NO: 25, and SEQ ID NO: 26.

13. The method of claim 8, wherein the alcohol in which the transformed microorganism exhibits higher tolerance as compared to parental microorganism is one of ethanol, propanol, and butanol.

14. The transformed microorganism produced by the method of claim 8.

15. An expression vector comprising a promoter and a heterologous polynucleotide, wherein said heterologous polynucleotide encodes one or more proteins, the one or more proteins being at least one of PntA and PntB, wherein each of PntA and PntB is a component protein of a dihydronicotinamide-adenine dinucleotide phosphate (NADPH) transhydrogenase complex, wherein the protein consists essentially of an amino acid sequence having at least 95% identity to one of SEQ ID NO: 23, SEQ ID NO: 24, SEQ ID NO: 25, and SEQ ID NO: 26, and wherein said promoter is operatively linked to said heterologous polynucleotide.

16. An expression vector comprising a promoter and a heterologous polynucleotide, wherein said heterologous polynucleotide encodes one or more proteins, the one or more proteins being at least one of PntA and PntB, wherein said heterologous polynucleotide comprises a nucleotide sequence having at least 95% identity to one of SEQ ID NO: 17, SEQ ID NO: 18, SEQ ID NO: 19, SEQ ID NO: 20, SEQ ID NO: 21, and SEQ ID NO: 22, wherein each of PntA and PntB is a component protein of a dihydronicotinamide-adenine dinucleotide phosphate (NADPH) transhydrogenase complex, and wherein said promoter is operatively linked to said heterologous polynucleotide.

17. The transformed microorganism of claim 4, wherein the alcohol in which the transformed microorganism exhibits its higher tolerance as compared to a non-transformed microorganism is one of ethanol, propanol, and butanol.

18. A microorganism comprising an alcohol tolerance gene, the alcohol tolerance gene being one of pntAB, pntA, and pntB, and wherein the microorganism is a progeny of the transformed microorganism of claim 4.

19. The method of claim 11, wherein the alcohol in which the transformed microorganism exhibits higher tolerance as compared to parental microorganism is one of ethanol, propanol, and butanol.

20. The transformed microorganism produced by the method of claim 11.

* * * * *

```
SEQUENCE LISTING

<160> NUMBER OF SEQ ID NOS: 26

<210> SEQ ID NO 1
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 1

ggggaccggt gaaaggagtt ttatggcaat t                                31


<210> SEQ ID NO 2
<211> LENGTH: 39
<212> TYPE: DNA
<213> ORGANISM: Artificial Sequence
<220> FEATURE:
<223> OTHER INFORMATION: Chemically Synthesized

<400> SEQUENCE: 2

ggggcctagg ttattgatta atatattctt ttgtcgaag                        39


<210> SEQ ID NO 3
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 3

accaactctt tttatttcct aggttattg                                   29


<210> SEQ ID NO 4
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 4

aggtcgcgac cggtgaaag                                              19


<210> SEQ ID NO 5
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 5

gggatagtaa ttcattcctg gttg                                        24


<210> SEQ ID NO 6
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 6

cgggcccgtt atttgtctat g                                           21
```

<210> SEQ ID NO 7
<211> LENGTH: 40
<212> TYPE: DNA
<213> ORGANISM: Artificial Sequence
<220> FEATURE:
<223> OTHER INFORMATION: Chemically Synthesized

<400> SEQUENCE: 7
taagaaggag atataccatg gcaattgtag tttccgctct 40

<210> SEQ ID NO 8
<211> LENGTH: 39
<212> TYPE: DNA
<213> ORGANISM: Artificial Sequence
<220> FEATURE:
<223> OTHER INFORMATION: Chemically Synthesied

<400> SEQUENCE: 8
gtggtggtgg tgctcgaatt attcagcctc ctttttatc 39

<210> SEQ ID NO 9
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 9
taagaaggag atataccatg agtactttag aaacgatcgc ct 42

<210> SEQ ID NO 10
<211> LENGTH: 43
<212> TYPE: DNA
<213> ORGANISM: Artificial Sequence
<220> FEATURE:
<223> OTHER INFORMATION: Chemically Synthesized

<400> SEQUENCE: 10
gtggtggtgg tgctcgaatt gattaatata ttcttttgtc gaa 43

<210> SEQ ID NO 11
<211> LENGTH: 41
<212> TYPE: DNA
<213> ORGANISM: Artificial Sequence
<220> FEATURE:
<223> OTHER INFORMATION: Chemically Synthesized

<400> SEQUENCE: 11
taagaaggag atataccatg tctacgatta ttgctgcttt g 41

<210> SEQ ID NO 12
<211> LENGTH: 38
<212> TYPE: DNA
<213> ORGANISM: Artificial Sequence
<220> FEATURE:
<223> OTHER INFORMATION: Chemically Synthesized

<400> SEQUENCE: 12
gtggtggtgg tgctcgaatc ccccttctca gctgattt 38

<210> SEQ ID NO 13
<211> LENGTH: 38
<212> TYPE: DNA
<213> ORGANISM: Artificial Sequence
<220> FEATURE:
<223> OTHER INFORMATION: Chemically Synthesized

<400> SEQUENCE: 13
taagaaggag atataccatg tcactcctta aaacgatt 38

<210> SEQ ID NO 14
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 14
gtggtggtgg tgctcgaaat ctaaataccc cttggtagcc gc 42

<210> SEQ ID NO 15
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 15
cccgcgaaat taatacgact cac 23

<210> SEQ ID NO 16
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 16
gcttcctttc gggctttgtt ag 22

<210> SEQ ID NO 17
<211> LENGTH: 3000
<212> TYPE: DNA
<213> ORGANISM: Oenococcus oeni

<400> SEQUENCE: 17
tcgtaaaaac gtttgcaaga aattgcgacg aaaggtgaat cgtgaaagga gttttatggc 60
aattgtagtt tccgctctaa aagaagctgc tggtgagaat cgtgtcgcat tgaccccga 120 tgttgtcgcc aagctggtta agagcaattt tgatgttgtt atcgaaaaag gagccggaga 180
aaaagcattt tattccgatg atgtttataa gagtgccggc gccaagttgt caaccagaac 240
agatgcttta aaagcagata tcgtgacggt cgtcaacgaa ccgtcgacgg caactttaaa 300
caaattgacg aaaggtcaaa caattattgg gatgttgaat cctttggggg acaaaaaagc 360
agttgaaagt ttagcgaagg ccggagttac ttctttagct ttcgaactgc ttccacgaac 420
ggtttcccgc gcccaaaatt tggatgcaaa ttcatcgcaa aaatcgattg caggatacaa 480
agcagctttg ttagctgctg atacttatcc gcaatatttt ccgatgatga tgacggcggc 540
cggaacggct cgtccggcta aagtacttgt tattggcgca gctgtcgctg gtttgcaggc 600
aatcggaact gctcatcgtt tgggggcggt agtttccggc tacgatatcc gtgaggatgc 660
tcgcggccag gttgaatcct taggagcaac ggctttgatt tccggcgttc aggtgaaaga 720
tgaaaatggc tatgctcgtg ctttgacaac agatgagaag aaagcgcagc agactgaact 780
ggaaggcttt attgctgaaa ataatgtcat tatcactaca gctcaagtac ctggtggaaa 840
gcctccggtc gtggtttcca aaaaagctgt agataatgct aaagccggaa cagtcttcat 900

```
cgatcttggt tcgtcagctc tcggcggtaa tgttgaaggt tccaagcctg gagagacagt    960
agtaactaaa agcggtgctt tgattgtggg cgccggtgat ttggcaagtc gtttgccaaa   1020
atcttcctct gacatgtatg cgaaaaacgt tcaaaataca attaattaca ttatcaagga   1080
tggaaaaatt ttgctcgatt tggacgatga tgttctaact gatctcgttg ctacttacaa   1140
aggagagatt tcttccaact tcttacggag ccgatttggt ttggaaaaac gtgttgctca   1200
gaaaaagacg gaagataaaa aggaggctga ataatgagtg aagaattata tgccaattta   1260
gcgatctttg ttttgagttt gctggttggt tttgaagtta tgtcgaagat cccttctacc   1320
ttgcaaacgc cgatgatgtc gggagcaaat gcgattcatg gagttgttgt cgtgggtgct   1380
tttgcgattg ccgccgaagc taataattgg cttctctata ttctggtctt ctttgctgcc   1440
ttatttgccg caatcaatgt ttccggaggc tatacagtca cggatcgtat gttgggcatg   1500
tttgatcgca aaccatccga caaaaaggag gcagataaat gagtacttta gaaacgatcg   1560
cctctttggt ttatcttgtt tcggcatttt gttatgtgat cggtgttcac ttaatgcgta   1620
gtccaaagac tgctaaaaat ggtaaccgtc tatcattcgt cggaatgatt ttagccgtta   1680
ttatgattct gtttcaatta atcagttccg gaagggttca agcgactgca tggattgtgt   1740
tgctggctgg cctgctgctt ggaataattt atggtgttat gcgggccaga aaagttccaa   1800
tgactgatgt cccgcaactt gtttctttgt ttaatgccgt tggtggcggt gctgctgctg   1860
ttattggtgt ttttgattat gtaactgcat ccggtcattt aagccttatt ttatcaattc   1920
cggttgtttt ggatgtaatc attggtggaa ttactttctc cggttctttg attgcaactg   1980
gtaaactttc cggaaaagtt tccgggaaac caattaattt ccctggtgca aaagtgatca   2040
atattttggt tgtaattgca attgtaattg ctgcctttct gatgatttct ggtacggaaa   2100
atccttggta tcttttgttg gctttgtttg ccagcctgat tttcggtctg ttgatgactc   2160
tgccgattgg tggtgctgac atgccggtgg ttgtttcttt actgaatgct tttactggtt   2220
tagcagtggc ttttgccggc tttgtaattg ataatcaggt tttgattatt gctggtgctt   2280
tagttggtgc cgccggtaca atcttgaccc tgcaaatggc cgatgcaatg aaccgttcgg   2340
tggcgaatat tttggctggt ggttttggaa ccggcgattc ggagtcttct tcggcctccg   2400
atggagcccc ggttaaagtt acagaaactt cggctgatga tattggcctt cagctggctt   2460
atgctcacaa tgtgatgatt gttcccggtt atgggcttgc tgccgcccag gcacaacatg   2520
aagtggccga attggcaaaa ctgttgactg ataatggcat taatgttgac tatgcgattc   2580
acccggttgc tggtcgtatg ccgggacaca tgaatgtttt actggctgat gtcaatgttc   2640
cttatggcca gctgaaacag cttgatgatg caaattcaat gtttaccaat acggacgttt   2700
ctttggtaat tggtgcaaac gatgttacca atccgttggc tcgcgagtcc ggtaatccaa   2760
tttctggaat gccaatcctc gatgttgaca agtcaaaatc ggttgttgtt attaagcgtt   2820
caatgagcac tggttacgcc ggcgttcaaa atccgttatt ctccttggat aacacaaaaa   2880
tgttcttcgc cgatgccaag aaaggtcttc aggacattat cgcttcgaca aaagaatata   2940
ttaatcaata attgattaat ataaatatta ttaaaatcgt cttttactga agacgatttt   3000
```

<210> SEQ ID NO 18
<211> LENGTH: 1176
<212> TYPE: DNA
<213> ORGANISM: Oenococcus oeni

<400> SEQUENCE: 18

```
atggcaattg tagtttccgc tctaaaagaa gctgctggtg agaatcgtgt cgcattgacc     60
```

```
cccgatgttg tcgccaagct ggttaagagc aattttgatg ttgttatcga aaaaggagcc    120

ggagaaaaag cattttattc cgatgatgtt tataagagtg ccggcgccaa gttgtcaacc    180

agaacagatg ctttaaaagc agatatcgtg acggtcgtca acgaaccgtc gacggcaact    240

ttaaacaaat tgacgaaagg tcaaacaatt attgggatgt tgaatccttt gggggacaaa    300

aaagcagttg aaagtttagc gaaggccgga gttacttctt tagctttcga actgcttcca    360

cgaacggttt cccgcgccca aaatttggat gcaaattcat cgcaaaaatc gattgcagga    420

tacaaagcag ctttgttagc tgctgatact tatccgcaat attttccgat gatgatgacg    480

gcggccggaa cggctcgtcc ggctaaagta cttgttattg gcgcagctgt cgctggtttg    540

caggcaatcg gaactgctca tcgtttgggg gcggtagttt ccggctacga tatccgtgag    600

gatgctcgcg gccaggttga atccttagga gcaacggctt tgatttccgg cgttcaggtg    660

aaagatgaaa atggctatgc tcgtgctttg acaacagatg agaagaaagc gcagcagact    720

gaactggaag gctttattgc tgaaaataat gtcattatca ctacagctca agtacctggt    780

ggaaagcctc cggtcgtggt ttccaaaaaa gctgtagata atgctaaagc cggaacagtc    840

ttcatcgatc ttggttcgtc agctctcggc ggtaatgttg aaggttccaa gcctggagag    900

acagtagtaa ctaaaagcgg tgctttgatt gtgggcgccg gtgatttggc aagtcgtttg    960

ccaaaatctt cctctgacat gtatgcgaaa aacgttcaaa atacaattaa ttacattatc   1020

aaggatggaa aaattttgct cgatttggac gatgatgttc taactgatct cgttgctact   1080

tacaaaggag agatttcttc caacttctta cggagccgat ttggtttgga aaaacgtgtt   1140

gctcagaaaa agacggaaga taaaaaggag gctgaa                             1176
```

```
<210> SEQ ID NO 19
<211> LENGTH: 1410
<212> TYPE: DNA
<213> ORGANISM: Oenococcus oeni

<400> SEQUENCE: 19
```

```
atgagtactt tagaaacgat cgcctctttg gtttatcttg tttcggcatt ttgttatgtg     60

atcggtgttc acttaatgcg tagtccaaag actgctaaaa atggtaaccg tctatcattc    120

gtcggaatga ttttagccgt tattatgatt ctgtttcaat taatcagttc cggaagggtt    180

caagcgactg catggattgt gttgctggct ggcctgctgc ttggaataat ttatggtgtt    240

atgcgggcca gaaaagttcc aatgactgat gtcccgcaac ttgtttcttt gtttaatgcc    300

gttggtggcg gtgctgctgc tgttattggt gtttttgatt atgtaactgc atccggtcat    360

ttaagcctta ttttatcaat tccggttgtt ttggatgtaa tcattggtgg aattactttc    420

tccggttctt tgattgcaac tggtaaactt tccggaaaag tttccgggaa accaattaat    480

ttccctggtg caaaagtgat caatattttg gttgtaattg caattgtaat tgctgccttt    540

ctgatgattt ctggtacgga aaatccttgg tatcttttgt tggctttgtt tgccagcctg    600

attttcggtc tgttgatgac tctgccgatt ggtggtgctg acatgccggt ggttgtttct    660

ttactgaatg cttttactgg tttagcagtg gcttttgccg gctttgtaat tgataatcag    720

gttttgatta ttgctggtgc tttagttggt gccgccggta caatcttgac cctgcaaatg    780

gccgatgcaa tgaaccgttc ggtggcgaat attttggctg gtggttttgg aaccggcgat    840

tcggagtctt cttcggcctc cgatggagcc ccggttaaag ttacagaaac ttcggctgat    900

gatattggcc ttcagctggc ttatgctcac aatgtgatga ttgttcccgg ttatgggctt    960
```

gctgccgccc aggcacaaca tgaagtggcc gaattggcaa aactgttgac tgataatggc 1020
attaatgttg actatgcgat tcacccggtt gctggtcgta tgccgggaca catgaatgtt 1080
ttactggctg atgtcaatgt tccttatggc cagctgaaac agcttgatga tgcaaattca 1140
atgtttacca atacggacgt ttctttggta attggtgcaa acgatgttac caatccgttg 1200
gctcgcgagt ccggtaatcc aatttctgga atgccaatcc tcgatgttga caagtcaaaa 1260
tcggttgttg ttattaagcg ttcaatgagc actggttacg ccggcgttca aaatccgtta 1320
ttctccttgg ataacacaaa aatgttcttc gccgatgcca agaaaggtct tcaggacatt 1380
atcgcttcga caaaagaata tattaatcaa 1410

<210> SEQ ID NO 20
<211> LENGTH: 2953
<212> TYPE: DNA
<213> ORGANISM: Lactobacillus buchneri

<400> SEQUENCE: 20
atgtctacga ttattgctgc tttgaaggaa tctggcgatg aaaaccgtgt ggcaatcaca 60
ccggatgtgg ctgcgaaatt agttcacagc aagtttgaag ttatgatcga acagggcgct 120
ggtcagaatg cttatttttc tgaccaggcc taccaagatg ctggcgcaaa agtcgttagc 180
cgagacgatg cagttagtca ggccaatgtg attgcgacgg ttgatttacc tgattcagag 240
actttgggca agttgcatga gggacagatt ttaattggct tgttgaaggc cttgaccgat 300
ttggactcgg tgcaaaaact tgctaaacag aaggtcacgg cgctgtcgtt tgaactgctg 360
ccgcggacca tttcccgtgc ccaaagcatg aatgtcttaa gttcacaagc ctcaattgcc 420
ggttacaaag ctgctttggt ggctgctgac aaattcgccc gttatttccc aatgatgatc 480
actgctgcgg ggactgccaa gcctgccaaa gtgttggtct tagggaccgg agttgccggc 540
ctgcaagcca ttggaactgc caaacggctg ggggcaattg tttccggtta tgatgttcgt 600
ccagcgtctc gaggcgaagt tgaatcactc ggtgccgaat ttctcactag ttcagtcagt 660
gctgtcggtg aaggcggtta tgcccgtcaa ttgtctgctg atgagcaaaa gcagcagcaa 720
gacgaattaa ttgggtttat caaacaaaat gatattgtca tcaccaccgc gcaggttcct 780
ggaagaaagc cgccactgct ggttcctcaa gccgccgttg ataacgctaa accaggtagc 840
gtcttcgttg atttggctgc cagtgatttg ggtggtaatg tcgctggatc aaagcccgac 900
caaacagtga tcactgattc cggtgttcaa ctgattgggg ccgggaattt agccagtgaa 960
atggcaacgt cggcttctga aatgttctct aagaacgttc aggcagtgat taatgatgtt 1020
gctgataagg atgctcaaat taccatcgat ttaaaagatg acgtaatgag ccaattggtt 1080
gcgaccgacc atggcgaaat tatttctgaa cgagtcagaa aagcgctgaa cctgccaatt 1140
tcaaaaccgg ctgaagacga tgctgcccct gccgattctg acgacaaatc agctgagaag 1200
ggggattagt cattatgagt caagaattat atacgaattt agccattttt gttttgagcc 1260
tgctagttgg gtttgaagtt atgagtaaaa ttccctcaac cctgcagacg ccaatgatgt 1320
ctggtgccaa tgcgattcat ggcgtcgtcg ttgtcggtgc ctttgtgatt gctgcagaag 1380
ccagcagctg gtatttctac ctgttggcat ttctagccgc attctttgca gctgtcaacg 1440
tcgccggtgg ttacaccgtg actgaccgga tgctgggaat gtttaaccgg ccgaaaaaac 1500
agccgaattc agctgacaag ggaggcgaca aataatgtca ctccttaaaa cgattgcttc 1560
cctaatttac ctgctgtcag cggtctgcta tgtgattggt gttcacatga tgcgctcccc 1620
aaagacggct cggaatggta atttactttc cggacttggg atggccatgg cagttgtcat 1680

```
gattttagtt gaaattatct ccaagggtca gattacctta attggctgga cggtattgtt   1740

tgcgggtctg ttaatcggaa ttttgtatgg agttatccgc gcacgcaaag tgccaatgac   1800

cgatgttcct caattggttt cgctgtttaa cgccgttggt ggcggtgccg ctgccacaat   1860

cgggattttc gattacaccc acgaagctgt cggtacctct ttgagcctgg ccttttccat   1920

tccagtgctg cttgacatta ttattggtgg gattaccttc tcaggctcgc taattgcaac   1980

cggtaaattg tccggacatg tgcccggcaa accaatttcg tttcccggcg acaaattgat   2040

taacggtctg gcagtgttag caattatcgt tgccggtgtt tggatgattg gttttccttc   2100

cgcttactgg cctatggtac tggcattgtt agccagtttg atttttggcc tattgatgac   2160

cttgccaatt ggtggtgccg acatgccggt ggttgtttca cttttgaacg cctttaccgg   2220

tttggcggtt gcctttgccg gatttgtcat tgataatcag gtcttgatta tcgctggtgc   2280

gctggttggt gcggccggaa caattttgac cctgcaaatg gccgaagcaa tgaaccgatc   2340

agttgccaac attattgctg gcggcttcgg tagtggcgat tccaacggca gtattggtgc   2400

gggtgctgag gtgccaacca acattaagaa gaccacaccc gatgatgtcg gcatgcagct   2460

ggcctatgcg cacaatgtca tgatcgttcc cggttatggt ttggctgccg ctcaggctca   2520

gcatgaagtc gctgagttgg cgaaattgct gacggatgcc ggaattaacg tcaactatgc   2580

gattcaccca gttgccggcc ggatgcctgg ccatatgaac gttttgctcg ccgatgtcaa   2640

cgttccttac gatcaaatga aacagttgga tgaagccaac tcgatgtttg aaaatactga   2700

cgtttcgctg gttattggcg ctaacgatgt taccaatcca ttggctcgtg aaaagggtaa   2760

cgccatttcg ggatgccaa ttttggatgt tgataaatca aagtccgtcg ttgtcattaa   2820

gcgttccatg agtaccggtt acgccggtgt tcaaaaccca ctgtttagtg aagatcagac   2880

cagtatgatg ttctcggatg ccaagaaggg gctgcaggaa attattgcgg ctaccaaggg   2940

gtatttagat taa                                                      2953
```

<210> SEQ ID NO 21
<211> LENGTH: 1205
<212> TYPE: DNA
<213> ORGANISM: Lactobacillus buchneri

<400> SEQUENCE: 21

```
atgtctacga ttattgctgc tttgaaggaa tctggcgatg aaaaccgtgt ggcaatcaca     60

ccggatgtgg ctgcgaaatt agttcacagc aagtttgaag ttatgatcga acagggcgct    120

ggtcagaatg cttattttc tgaccaggcc taccaagatg ctggcgcaaa agtcgttagc    180

cgagacgatg cagttagtca ggccaatgtg attgcgacgg ttgatttacc tgattcagag    240

actttgggca agttgcatga gggacagatt ttaattggct tgttgaaggc cttgaccgat    300

ttggactcgg tgcaaaaact tgctaaacag aaggtcacgg cgctgtcgtt tgaactgctg    360

ccgcggacca tttcccgtgc ccaaagcatg aatgtcttaa gttcacaagc ctcaattgcc    420

ggttacaaag ctgctttggt ggctgctgac aaattcgccc gttatttccc aatgatgatc    480

actgctgcgg ggactgccaa gcctgccaaa gtgttggtct tagggaccgg agttgccggc    540

ctgcaagcca ttggaactgc caaacggctg ggggcaattg tttccggtta tgatgttcgt    600

ccagcgtctc gaggcgaagt tgaatcactc ggtgccgaat ttctcactag ttcagtcagt    660

gctgtcggtg aaggcggtta tgcccgtcaa ttgtctgctg atgagcaaaa gcagcagcaa    720

gacgaattaa ttgggtttat caaacaaaat gatattgtca tcaccaccgc gcaggttcct    780
```

```
ggaagaaagc cgccactgct ggttcctcaa gccgccgttg ataacgctaa accaggtagc    840

gtcttcgttg atttggctgc cagtgatttg ggtggtaatg tcgctggatc aaagcccgac    900

caaacagtga tcactgattc cggtgttcaa ctgattgggg ccgggaattt agccagtgaa    960

atggcaacgt cggcttctga aatgttctct aagaacgttc aggcagtgat taatgatgtt   1020

gctgataagg atgctcaaat taccatcgat ttaaaagatg acgtaatgag ccaattggtt   1080

gcgaccgacc atggcgaaat tatttctgaa cgagtcagaa aagcgctgaa cctgccaatt   1140

tcaaaaccgg ctgaagacga tgctgcccct gccgattctg acgacaaatc agctgagaag   1200

gggga                                                               1205
```

<210> SEQ ID NO 22
<211> LENGTH: 1416
<212> TYPE: DNA
<213> ORGANISM: Lactobacillus buchneri

<400> SEQUENCE: 22

```
atgtcactcc ttaaaacgat tgcttcccta atttacctgc tgtcagcggt ctgctatgtg     60

attggtgttc acatgatgcg ctccccaaag acggctcgga atggtaattt actttccgga    120

cttgggatgg ccatggcagt tgtcatgatt ttagttgaaa ttatctccaa gggtcagatt    180

accttaattg gctggacggt attgtttgcg ggtctgttaa tcggaatttt gtatggagtt    240

atccgcgcac gcaaagtgcc aatgaccgat gttcctcaat tggtttcgct gtttaacgcc    300

gttggtggcg gtgccgctgc cacaatcggg attttcgatt acacccacga agctgtcggt    360

acctctttga gcctggcctt ttccattcca gtgctgcttg acattattat tggtgggatt    420

accttctcag gctcgctaat tgcaaccggt aaattgtccg gacatgtgcc cggcaaacca    480

atttcgtttc ccggcgacaa attgattaac ggtctggcag tgttagcaat tatcgttgcc    540

ggtgtttgga tgattggttt tccttccgct tactggccta tggtactggc attgttagcc    600

agtttgattt ttggcctatt gatgaccttg ccaattggtg gtgccgacat gccggtggtt    660

gtttcacttt tgaacgcctt taccggtttg gcggttgcct ttgccggatt tgtcattgat    720

aatcaggtct tgattatcgc tggtgcgctg gttggtgcgg ccggaacaat tttgaccctg    780

caaatggccg aagcaatgaa ccgatcagtt gccaacatta ttgctggcgg cttcggtagt    840

ggcgattcca acggcagtat tggtgcgggt gctgaggtgc caaccaacat taagaagacc    900

acacccgatg atgtcggcat gcagctggcc tatgcgcaca atgtcatgat cgttcccggt    960

tatggtttgg ctgccgctca ggctcagcat gaagtcgctg agttggcgaa attgctgacg   1020

gatgccggaa ttaacgtcaa ctatgcgatt cacccagttg ccggccggat gcctggccat   1080

atgaacgttt tgctcgccga tgtcaacgtt ccttacgatc aaatgaaaca gttggatgaa   1140

gccaactcga tgtttgaaaa tactgacgtt tcgctggtta ttggcgctaa cgatgttacc   1200

aatccattgg ctcgtgaaaa gggtaacgcc atttcgggga tgccaatttt ggatgttgat   1260

aaatcaaagt ccgtcgttgt cattaagcgt tccatgagta ccggttacgc cggtgttcaa   1320

aacccactgt ttagtgaaga tcagaccagt atgatgttct cggatgccaa gaaggggctg   1380

caggaaatta ttgcggctac caaggggtat ttagat                             1416
```

<210> SEQ ID NO 23
<211> LENGTH: 392
<212> TYPE: PRT
<213> ORGANISM: Oenococcus oeni

<400> SEQUENCE: 23

```
Met Ala Ile Val Val Ser Ala Leu Lys Glu Ala Ala Gly Glu Asn Arg
1               5                   10                  15

Val Ala Leu Thr Pro Asp Val Val Ala Lys Leu Val Lys Ser Asn Phe
            20                  25                  30

Asp Val Val Ile Glu Lys Gly Ala Gly Glu Lys Ala Phe Tyr Ser Asp
        35                  40                  45

Asp Val Tyr Lys Ser Ala Gly Ala Lys Leu Ser Thr Arg Thr Asp Ala
    50                  55                  60

Leu Lys Ala Asp Ile Val Thr Val Val Asn Glu Pro Ser Thr Ala Thr
65                  70                  75                  80

Leu Asn Lys Leu Thr Lys Gly Gln Thr Ile Ile Gly Met Leu Asn Pro
                85                  90                  95

Leu Gly Asp Lys Lys Ala Val Glu Ser Leu Ala Lys Ala Gly Val Thr
            100                 105                 110

Ser Leu Ala Phe Glu Leu Leu Pro Arg Thr Val Ser Arg Ala Gln Asn
        115                 120                 125

Leu Asp Ala Asn Ser Ser Gln Lys Ser Ile Ala Gly Tyr Lys Ala Ala
    130                 135                 140

Leu Leu Ala Ala Asp Thr Tyr Pro Gln Tyr Phe Pro Met Met Met Thr
145                 150                 155                 160

Ala Ala Gly Thr Ala Arg Pro Ala Lys Val Leu Val Ile Gly Ala Ala
                165                 170                 175

Val Ala Gly Leu Gln Ala Ile Gly Thr Ala His Arg Leu Gly Ala Val
            180                 185                 190

Val Ser Gly Tyr Asp Ile Arg Glu Asp Ala Arg Gly Gln Val Glu Ser
        195                 200                 205

Leu Gly Ala Thr Ala Leu Ile Ser Gly Val Gln Val Lys Asp Glu Asn
    210                 215                 220

Gly Tyr Ala Arg Ala Leu Thr Thr Asp Glu Lys Lys Ala Gln Gln Thr
225                 230                 235                 240

Glu Leu Glu Gly Phe Ile Ala Glu Asn Asn Val Ile Ile Thr Thr Ala
                245                 250                 255

Gln Val Pro Gly Gly Lys Pro Pro Val Val Val Ser Lys Lys Ala Val
            260                 265                 270

Asp Asn Ala Lys Ala Gly Thr Val Phe Ile Asp Leu Gly Ser Ser Ala
        275                 280                 285

Leu Gly Gly Asn Val Glu Gly Ser Lys Pro Gly Glu Thr Val Val Thr
    290                 295                 300

Lys Ser Gly Ala Leu Ile Val Gly Ala Gly Asp Leu Ala Ser Arg Leu
305                 310                 315                 320

Pro Lys Ser Ser Ser Asp Met Tyr Ala Lys Asn Val Gln Asn Thr Ile
                325                 330                 335

Asn Tyr Ile Ile Lys Asp Gly Lys Ile Leu Leu Asp Leu Asp Asp Asp
            340                 345                 350

Val Leu Thr Asp Leu Val Ala Thr Tyr Lys Gly Glu Ile Ser Ser Asn
        355                 360                 365

Phe Leu Arg Ser Arg Phe Gly Leu Glu Lys Arg Val Ala Gln Lys Lys
    370                 375                 380

Thr Glu Asp Lys Lys Glu Ala Glu
385                 390
```

<210> SEQ ID NO 24
<211> LENGTH: 470

```
<212> TYPE: PRT
<213> ORGANISM: Oenococcus oeni

<400> SEQUENCE: 24

Met Ser Thr Leu Glu Thr Ile Ala Ser Leu Val Tyr Leu Val Ser Ala
1               5                   10                  15

Phe Cys Tyr Val Ile Gly Val His Leu Met Arg Ser Pro Lys Thr Ala
            20                  25                  30

Lys Asn Gly Asn Arg Leu Ser Phe Val Gly Met Ile Leu Ala Val Ile
        35                  40                  45

Met Ile Leu Phe Gln Leu Ile Ser Ser Gly Arg Val Gln Ala Thr Ala
    50                  55                  60

Trp Ile Val Leu Leu Ala Gly Leu Leu Leu Gly Ile Ile Tyr Gly Val
65                  70                  75                  80

Met Arg Ala Arg Lys Val Pro Met Thr Asp Val Pro Gln Leu Val Ser
                85                  90                  95

Leu Phe Asn Ala Val Gly Gly Gly Ala Ala Ala Val Ile Gly Val Phe
            100                 105                 110

Asp Tyr Val Thr Ala Ser Gly His Leu Ser Leu Ile Leu Ser Ile Pro
        115                 120                 125

Val Val Leu Asp Val Ile Ile Gly Gly Ile Thr Phe Ser Gly Ser Leu
    130                 135                 140

Ile Ala Thr Gly Lys Leu Ser Gly Lys Val Ser Gly Lys Pro Ile Asn
145                 150                 155                 160

Phe Pro Gly Ala Lys Val Ile Asn Ile Leu Val Val Ile Ala Ile Val
                165                 170                 175

Ile Ala Ala Phe Leu Met Ile Ser Gly Thr Glu Asn Pro Trp Tyr Leu
            180                 185                 190

Leu Leu Ala Leu Phe Ala Ser Leu Ile Phe Gly Leu Leu Met Thr Leu
        195                 200                 205

Pro Ile Gly Gly Ala Asp Met Pro Val Val Val Ser Leu Leu Asn Ala
    210                 215                 220

Phe Thr Gly Leu Ala Val Ala Phe Ala Gly Phe Val Ile Asp Asn Gln
225                 230                 235                 240

Val Leu Ile Ile Ala Gly Ala Leu Val Gly Ala Ala Gly Thr Ile Leu
                245                 250                 255

Thr Leu Gln Met Ala Asp Ala Met Asn Arg Ser Val Ala Asn Ile Leu
            260                 265                 270

Ala Gly Gly Phe Gly Thr Gly Asp Ser Glu Ser Ser Ser Ala Ser Asp
        275                 280                 285

Gly Ala Pro Val Lys Val Thr Glu Thr Ser Ala Asp Asp Ile Gly Leu
    290                 295                 300

Gln Leu Ala Tyr Ala His Asn Val Met Ile Val Pro Gly Tyr Gly Leu
305                 310                 315                 320

Ala Ala Ala Gln Ala Gln His Glu Val Ala Glu Leu Ala Lys Leu Leu
                325                 330                 335

Thr Asp Asn Gly Ile Asn Val Asp Tyr Ala Ile His Pro Val Ala Gly
            340                 345                 350

Arg Met Pro Gly His Met Asn Val Leu Leu Ala Asp Val Asn Val Pro
        355                 360                 365

Tyr Gly Gln Leu Lys Gln Leu Asp Asp Ala Asn Ser Met Phe Thr Asn
    370                 375                 380

Thr Asp Val Ser Leu Val Ile Gly Ala Asn Asp Val Thr Asn Pro Leu
385                 390                 395                 400
```

```
Ala Arg Glu Ser Gly Asn Pro Ile Ser Gly Met Pro Ile Leu Asp Val
                405                 410                 415

Asp Lys Ser Lys Ser Val Val Val Ile Lys Arg Ser Met Ser Thr Gly
            420                 425                 430

Tyr Ala Gly Val Gln Asn Pro Leu Phe Ser Leu Asp Asn Thr Lys Met
        435                 440                 445

Phe Phe Ala Asp Ala Lys Lys Gly Leu Gln Asp Ile Ile Ala Ser Thr
    450                 455                 460

Lys Glu Tyr Ile Asn Gln
465                 470


<210> SEQ ID NO 25
<211> LENGTH: 402
<212> TYPE: PRT
<213> ORGANISM: Lactobacillus buchneri

<400> SEQUENCE: 25

Met Ser Thr Ile Ile Ala Ala Leu Lys Glu Ser Gly Asp Glu Asn Arg
1               5                   10                  15

Val Ala Ile Thr Pro Asp Val Ala Ala Lys Leu Val His Ser Lys Phe
            20                  25                  30

Glu Val Met Ile Glu Gln Gly Ala Gly Gln Asn Ala Tyr Phe Ser Asp
        35                  40                  45

Gln Ala Tyr Gln Asp Ala Gly Ala Lys Val Val Ser Arg Asp Asp Ala
    50                  55                  60

Val Ser Gln Ala Asn Val Ile Ala Thr Val Asp Leu Pro Asp Ser Glu
65                  70                  75                  80

Thr Leu Gly Lys Leu His Glu Gly Gln Ile Leu Ile Gly Leu Leu Lys
                85                  90                  95

Ala Leu Thr Asp Leu Asp Ser Val Gln Lys Leu Ala Lys Gln Lys Val
            100                 105                 110

Thr Ala Leu Ser Phe Glu Leu Leu Pro Arg Thr Ile Ser Arg Ala Gln
        115                 120                 125

Ser Met Asn Val Leu Ser Ser Gln Ala Ser Ile Ala Gly Tyr Lys Ala
    130                 135                 140

Ala Leu Val Ala Ala Asp Lys Phe Ala Arg Tyr Phe Pro Met Met Ile
145                 150                 155                 160

Thr Ala Ala Gly Thr Ala Lys Pro Ala Lys Val Leu Val Leu Gly Thr
                165                 170                 175

Gly Val Ala Gly Leu Gln Ala Ile Gly Thr Ala Lys Arg Leu Gly Ala
            180                 185                 190

Ile Val Ser Gly Tyr Asp Val Arg Pro Ala Ser Arg Gly Glu Val Glu
        195                 200                 205

Ser Leu Gly Ala Glu Phe Leu Thr Ser Ser Val Ser Ala Val Gly Glu
    210                 215                 220

Gly Gly Tyr Ala Arg Gln Leu Ser Ala Asp Glu Gln Lys Gln Gln Gln
225                 230                 235                 240

Asp Glu Leu Ile Gly Phe Ile Lys Gln Asn Asp Ile Val Ile Thr Thr
                245                 250                 255

Ala Gln Val Pro Gly Arg Lys Pro Pro Leu Leu Val Pro Gln Ala Ala
            260                 265                 270

Val Asp Asn Ala Lys Pro Gly Ser Val Phe Val Asp Leu Ala Ala Ser
        275                 280                 285

Asp Leu Gly Gly Asn Val Ala Gly Ser Lys Pro Asp Gln Thr Val Ile
```

```
    290                 295                 300

Thr Asp Ser Gly Val Gln Leu Ile Gly Ala Gly Asn Leu Ala Ser Glu
305                 310                 315                 320

Met Ala Thr Ser Ala Ser Glu Met Phe Ser Lys Asn Val Gln Ala Val
                325                 330                 335

Ile Asn Asp Val Ala Asp Lys Asp Ala Gln Ile Thr Ile Asp Leu Lys
            340                 345                 350

Asp Asp Val Met Ser Gln Leu Val Ala Thr Asp His Gly Glu Ile Ile
        355                 360                 365

Ser Glu Arg Val Arg Lys Ala Leu Asn Leu Pro Ile Ser Lys Pro Ala
    370                 375                 380

Glu Asp Asp Ala Ala Pro Ala Asp Ser Asp Asp Lys Ser Ala Glu Lys
385                 390                 395                 400

Gly Asp


<210> SEQ ID NO 26
<211> LENGTH: 472
<212> TYPE: PRT
<213> ORGANISM: Lactobacillus buchneri

<400> SEQUENCE: 26

Met Ser Leu Leu Lys Thr Ile Ala Ser Leu Ile Tyr Leu Leu Ser Ala
1               5                   10                  15

Val Cys Tyr Val Ile Gly Val His Met Met Arg Ser Pro Lys Thr Ala
            20                  25                  30

Arg Asn Gly Asn Leu Leu Ser Gly Leu Gly Met Ala Met Ala Val Val
        35                  40                  45

Met Ile Leu Val Glu Ile Ile Ser Lys Gly Gln Ile Thr Leu Ile Gly
    50                  55                  60

Trp Thr Val Leu Phe Ala Gly Leu Leu Ile Gly Ile Leu Tyr Gly Val
65                  70                  75                  80

Ile Arg Ala Arg Lys Val Pro Met Thr Asp Val Pro Gln Leu Val Ser
                85                  90                  95

Leu Phe Asn Ala Val Gly Gly Gly Ala Ala Ala Thr Ile Gly Ile Phe
            100                 105                 110

Asp Tyr Thr His Glu Ala Val Gly Thr Ser Leu Ser Leu Ala Phe Ser
        115                 120                 125

Ile Pro Val Leu Leu Asp Ile Ile Ile Gly Gly Ile Thr Phe Ser Gly
    130                 135                 140

Ser Leu Ile Ala Thr Gly Lys Leu Ser Gly His Val Pro Gly Lys Pro
145                 150                 155                 160

Ile Ser Phe Pro Gly Asp Lys Leu Ile Asn Gly Leu Ala Val Leu Ala
                165                 170                 175

Ile Ile Val Ala Gly Val Trp Met Ile Gly Phe Pro Ser Ala Tyr Trp
            180                 185                 190

Pro Met Val Leu Ala Leu Leu Ala Ser Leu Ile Phe Gly Leu Leu Met
        195                 200                 205

Thr Leu Pro Ile Gly Gly Ala Asp Met Pro Val Val Val Ser Leu Leu
    210                 215                 220

Asn Ala Phe Thr Gly Leu Ala Val Ala Phe Ala Gly Phe Val Ile Asp
225                 230                 235                 240

Asn Gln Val Leu Ile Ile Ala Gly Ala Leu Val Gly Ala Ala Gly Thr
                245                 250                 255

Ile Leu Thr Leu Gln Met Ala Glu Ala Met Asn Arg Ser Val Ala Asn
```

-continued

```
            260                 265                 270

Ile Ile Ala Gly Gly Phe Gly Ser Gly Asp Ser Asn Gly Ser Ile Gly
        275                 280                 285

Ala Gly Ala Glu Val Pro Thr Asn Ile Lys Lys Thr Thr Pro Asp Asp
    290                 295                 300

Val Gly Met Gln Leu Ala Tyr Ala His Asn Val Met Ile Val Pro Gly
305                 310                 315                 320

Tyr Gly Leu Ala Ala Ala Gln Ala Gln His Glu Val Ala Glu Leu Ala
                325                 330                 335

Lys Leu Leu Thr Asp Ala Gly Ile Asn Val Asn Tyr Ala Ile His Pro
            340                 345                 350

Val Ala Gly Arg Met Pro Gly His Met Asn Val Leu Leu Ala Asp Val
        355                 360                 365

Asn Val Pro Tyr Asp Gln Met Lys Gln Leu Asp Glu Ala Asn Ser Met
    370                 375                 380

Phe Glu Asn Thr Asp Val Ser Leu Val Ile Gly Ala Asn Asp Val Thr
385                 390                 395                 400

Asn Pro Leu Ala Arg Glu Lys Gly Asn Ala Ile Ser Gly Met Pro Ile
                405                 410                 415

Leu Asp Val Asp Lys Ser Lys Ser Val Val Val Ile Lys Arg Ser Met
            420                 425                 430

Ser Thr Gly Tyr Ala Gly Val Gln Asn Pro Leu Phe Ser Glu Asp Gln
        435                 440                 445

Thr Ser Met Met Phe Ser Asp Ala Lys Lys Gly Leu Gln Glu Ile Ile
    450                 455                 460

Ala Ala Thr Lys Gly Tyr Leu Asp
465                 470
```